(12) United States Patent
Sakanishi et al.

(10) Patent No.: US 12,195,442 B2
(45) Date of Patent: Jan. 14, 2025

(54) (HETERO)ARYLIMIDAZOLE COMPOUND AND HARMFUL ORGANISM CONTROL AGENT

(71) Applicant: Nippon Soda Co., Ltd., Tokyo (JP)

(72) Inventors: Keita Sakanishi, Kanagawa (JP); Norifumi Sakiyama, Kanagawa (JP); Hikaru Aoyama, Kanagawa (JP); Maki Matsui, Kanagawa (JP); Takao Iwasa, Kanagawa (JP); Tomomi Kobayashi, Kanagawa (JP); Daisuke Ushijima, Kanagawa (JP); Keita Azuma, Kanagawa (JP); Masanori Sumino, Kanagawa (JP); Yasuhiko Ashikari, Kanagawa (JP); Kotaro Shibayama, Kanagawa (JP); Riho Taguchi, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 631 days.

(21) Appl. No.: 17/286,888

(22) PCT Filed: Oct. 23, 2019

(86) PCT No.: PCT/JP2019/041540
§ 371 (c)(1),
(2) Date: Apr. 20, 2021

(87) PCT Pub. No.: WO2020/090585
PCT Pub. Date: May 7, 2020

(65) Prior Publication Data
US 2021/0380554 A1    Dec. 9, 2021

(30) Foreign Application Priority Data
Oct. 29, 2018   (JP) ................... 2018-202998

(51) Int. Cl.
C07D 401/04     (2006.01)
A01N 43/50      (2006.01)

(52) U.S. Cl.
CPC ........... *C07D 401/04* (2013.01); *A01N 43/50* (2013.01)

(58) Field of Classification Search
CPC ..................... C07D 401/04; A01N 43/50
See application file for complete search history.

(56) References Cited

U.S. PATENT DOCUMENTS

| | | | |
|---|---|---|---|
| 11,180,456 B2 * | 11/2021 | Hamamoto | C07D 403/12 |
| 2017/0342065 A1 | 11/2017 | Hueter et al. | |
| 2017/0362224 A1 | 12/2017 | Edmunds et al. | |
| 2018/0002347 A1 | 1/2018 | Yonemura et al. | |
| 2018/0362470 A1 | 12/2018 | Hamamoto et al. | |

FOREIGN PATENT DOCUMENTS

| | | |
|---|---|---|
| JP | 2018-507184 A | 3/2018 |
| JP | 2018-509379 A | 4/2018 |
| JP | 2019-019068 A | 2/2019 |
| WO | WO-2016/121997 A1 | 8/2016 |
| WO | WO-2017/016922 A1 | 2/2017 |
| WO | WO-2017/104741 A1 | 6/2017 |

* cited by examiner

*Primary Examiner* — Andrew S Rosenthal
*Assistant Examiner* — Danielle Kim
(74) *Attorney, Agent, or Firm* — Millen White Zelano & Branigan; Csaba Henter

(57) ABSTRACT

An object of the present invention is to provide a (hetero) aryl imidazole compound that is excellent in pest control activity, particularly, insecticidal activity and/or acaricidal activity, is excellent in safety, and may be industrially advantageously synthesized. The (hetero)aryl imidazole compound of the present invention is a compound represented by the formula (I)

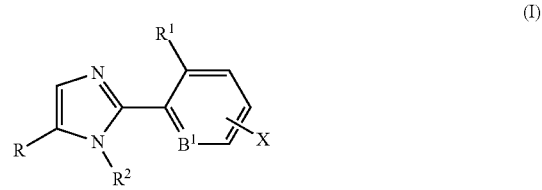

(I)

an N-oxide compound, stereoisomer, tautomer or hydrate thereof or a salt of any of these compounds. In the formula (I), $B^1$ represents a nitrogen atom or CH; X represents a substituted or unsubstituted C3-8 cycloalkyl group; $R^1$ represents a substituted or unsubstituted C1-6 alkylthio group or a substituted or unsubstituted C1-6 alkylsulfonyl group; $R^2$ represents a substituted or unsubstituted C1-6 alkyl group; and R represents a substituted or unsubstituted C2-6 alkenyl group.

10 Claims, No Drawings

(HETERO)ARYLIMIDAZOLE COMPOUND AND HARMFUL ORGANISM CONTROL AGENT

CROSS-REFERENCE TO RELATED APPLICATIONS

This application is the U.S. National Stage of PCT/JP2019/041540, filed Oct. 23, 2019, which claims priority to JP 2018-202998, filed Oct. 29, 2018.

TECHNICAL FIELD

The present invention relates to a (hetero)aryl imidazole compound and a pest control agent. More specifically, the present invention relates to a (hetero)aryl imidazole compound that has excellent insecticidal activity and/or acaricidal activity, is excellent in safety, and may be industrially advantageously synthesized, and a pest control agent containing it as an active ingredient.

The present application claims the priority of Japanese Patent Application No. 2018-202998 filed on Oct. 29, 2018, the contents of which are incorporated herein.

BACKGROUND ART

Various compounds having insecticidal or acaricidal activity have been proposed. For practical use of such compounds as agrochemicals, it is required not only to have sufficiently high efficacy but to be less likely to cause chemical resistance, to cause neither phytotoxicity to plants nor soil pollution, and to be low toxic to livestock, fishes, etc.

Patent document 1 discloses a compound represented by the formula (A), etc.

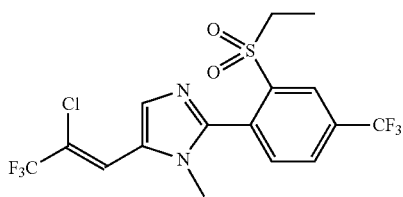

(A)

Patent document 2 discloses a compound represented by the formula (B), etc.

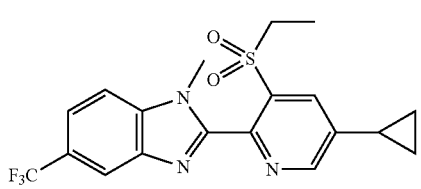

(B)

PRIOR ART DOCUMENTS

Patent Documents

Patent document 1: WO2017/104741A
Patent document 2: WO2016/121997A

SUMMARY OF THE INVENTION

Object to be Solved by the Invention

An object of the present invention is to provide a (hetero)aryl imidazole compound that is excellent in pest control activity, particularly, insecticidal activity and/or acaricidal activity, is excellent in safety, and may be industrially advantageously synthesized. Another object of the present invention is to provide a pest control agent, an insecticide or acaricide, an ectoparasite control agent, or an endoparasite control agent or expellant containing the (hetero)aryl imidazole compound as an active ingredient. A further object of the present invention is to provide a seed treatment agent, a vegetative propagation organ treatment agent, a granular agrochemical composition for paddy rice seedling nursery box treatment, a soil treatment agent, a bait agent, and a plant growth promoter containing the (hetero)aryl imidazole compound as an active ingredient.

Means to Solve the Object

As a result of diligent studies to attain the objects, the present invention including the following form has been completed.

[1] A compound represented by the formula (I), an N-oxide compound, stereoisomer, tautomer or hydrate thereof or a salt of any of these compounds:

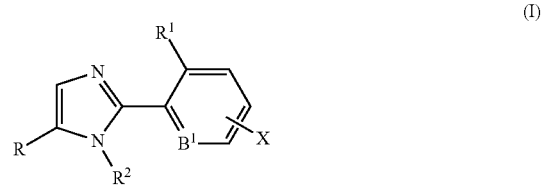

(I)

wherein
$B^1$ represents a nitrogen atom or CH;
X represents a substituted or unsubstituted C3-8 cycloalkyl group;
$R^1$ represents a substituted or unsubstituted C1-6 alkylthio group or a substituted or unsubstituted C1-6 alkylsulfonyl group;
$R^2$ represents a substituted or unsubstituted C1-6 alkyl group; and
R represents a substituted or unsubstituted C2-6 alkenyl group.

[2] The compound according to the above [1], an N-oxide compound, stereoisomer, tautomer or hydrate thereof or a salt of any one of these compounds, wherein the formula (I) is the formula (II):

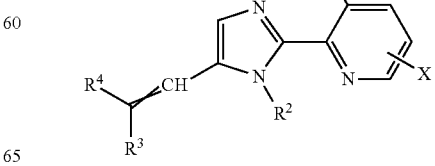

(II)

wherein
R¹, R², and X have the same meanings as described in the formula (I);
R³ represents a hydrogen atom or a halogeno group;
R⁴ represents a C1-4 haloalkyl group; and
the carbon-carbon double stereo bond represents an E form or a Z form, or a mixture thereof.

[3] A compound represented by any of the formula (III) to the formula (X), an N-oxide compound, stereoisomer, tautomer or hydrate thereof or a salt of any of these compounds:

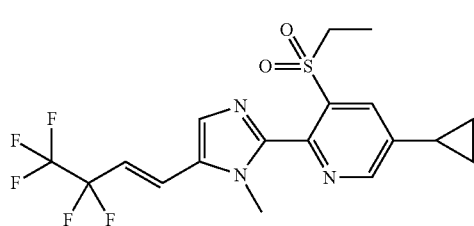
(III)

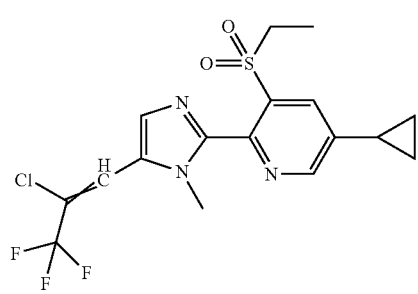
(IV)

wherein the carbon-carbon double stereo bond represents an E form or a Z form, or a mixture thereof;

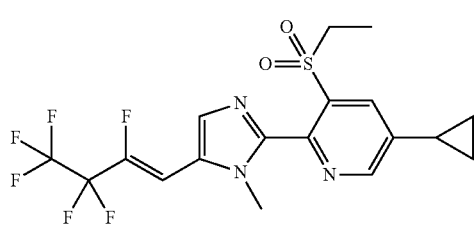
(V)

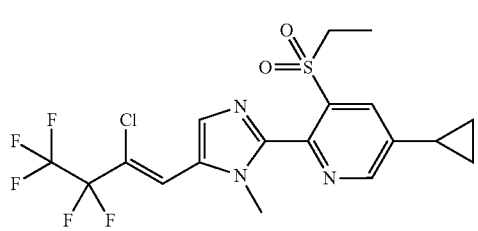
(VI)

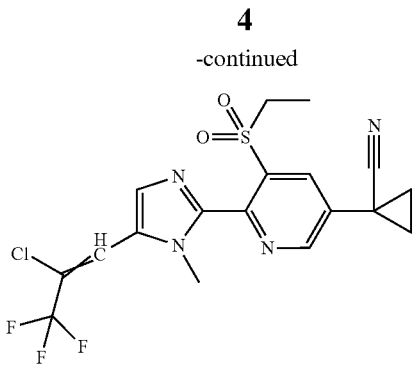
(VII)

wherein the carbon-carbon double stereo bond represents an E form or a Z form, or a mixture thereof;

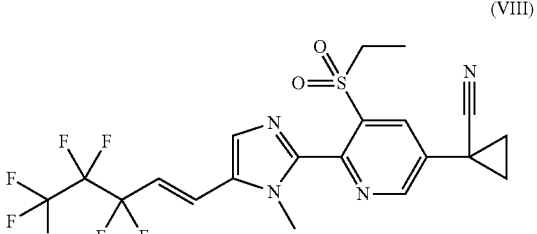
(VIII)

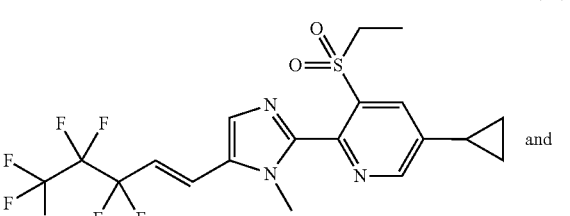
(IX) and

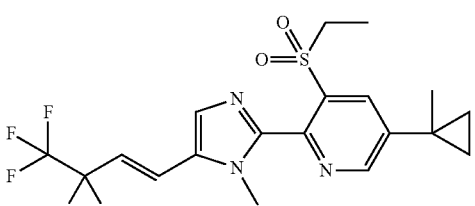
(X)

[4] A pest control agent comprising at least one compound selected from the group consisting of a compound according to any one of the above [1] to [3], an N-oxide compound, stereoisomer, tautomer and hydrate thereof and a salt of any of these compounds.

[5] An insecticide or acaricide comprising at least one compound selected from the group consisting of a compound according to any one of the above [1] to [3], an N-oxide compound, stereoisomer, tautomer and hydrate thereof and a salt of any of these compounds, as an active ingredient.

[6] An ectoparasite control agent comprising at least one compound selected from the group consisting of a compound according to any one of the above [1] to [3], an N-oxide compound, stereoisomer, tautomer and hydrate thereof and a salt of any of these compounds, as an active ingredient.

[7] An endoparasite control agent or expellant comprising at least one compound selected from the group consisting of a compound according to any one of the above [1] to [3], an N-oxide compound, stereoisomer, tautomer and hydrate thereof and a salt of any of these compounds, as an active ingredient.

[8] A seed treatment agent or vegetative propagation organ treatment agent comprising at least one compound selected from the group consisting of a compound according to any one of the above [1] to [3], an N-oxide compound, stereoisomer, tautomer and hydrate thereof and a salt of any of these compounds, as an active ingredient.

[9] A granular agrochemical composition for paddy rice seedling nursery box treatment comprising at least one compound selected from the group consisting of a compound according to any one of the above [1] to [3], an N-oxide compound, stereoisomer, tautomer and hydrate thereof and a salt of any of these compounds, as an active ingredient.

[10] A soil treatment agent comprising at least one compound selected from the group consisting of a compound according to any one of the above [1] to [3], an N-oxide compound, stereoisomer, tautomer and hydrate thereof and a salt of any of these compounds, as an active ingredient.

[11] A bait agent comprising at least one compound selected from the group consisting of a compound according to any one of the above [1] to [3], an N-oxide compound, stereoisomer, tautomer and hydrate thereof and a salt of any of these compounds, as an active ingredient.

[12] A plant growth promoter comprising at least one compound selected from the group consisting of a compound according to any one of the above [1] to [3], an N-oxide compound, stereoisomer, tautomer and hydrate thereof and a salt of any of these compounds, as an active ingredient.

Effect of the Invention

The (hetero)aryl imidazole compound of the present invention may control pests that are problems associated with crops or hygiene. Particularly, the (hetero)aryl imidazole compound of the present invention may effectively control agricultural insect pests and acari at a lower concentration. Furthermore, the (hetero)aryl imidazole compound of the present invention may effectively control ectoparasites and endoparasites harmful to humans and animals.

Also, the (hetero)aryl imidazole compound of the present invention may be used as a seed treatment agent, a vegetative propagation organ treatment agent, a granular agrochemical composition for paddy rice seedling nursery box treatment, a soil treatment agent, a bait agent, or a plant growth promoter.

MODE OF CARRYING OUT THE INVENTION

[(Hetero)aryl Imidazole Compound]

The (hetero)aryl imidazole compound of the present invention is a compound represented by the formula (I) (hereinafter, also referred to as compound (I)), an N-oxide compound, stereoisomer, tautomer or hydrate thereof or a salt of any of these compounds. The compound represented by the formula (I) includes every stereoisomer which is an enantiomer or a diastereomer.

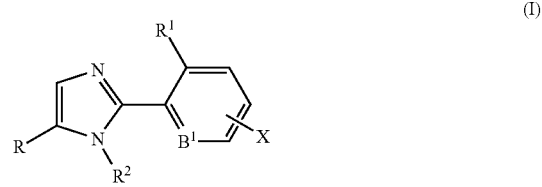

In the present invention, the term "unsubstituted" means a group consisting of only a mother nucleus. Only the name of a group consisting of a mother nucleus without the term "substituted" means an "unsubstituted" group unless otherwise specified.

On the other hand, the term "substituted" means that any hydrogen atom of a group consisting of a mother nucleus is substituted with a group (substituent) having a structure that is the same as or different from that of the mother nucleus. Thus, the "substituent" means another group bonded to the group consisting of a mother nucleus. The number of the substituent may be one or more. Two or more substituents are the same or different.

Terms such as "C1-6" mean that the number of carbon atoms in the group consisting of a mother nucleus is 1 to 6, etc. This number of carbon atoms does not include the number of carbon atoms present in the substituent. For example, a butyl group having an ethoxy group as a substituent is classified into a C2 alkoxy C4 alkyl group.

The "substituent" is not particularly limited as long as the substituent is chemically acceptable and produces the effect of the present invention. Hereinafter, a group capable of serving as the "substituent" is exemplified:

a C1-6 alkyl group such as a methyl group, an ethyl group, a n-propyl group, an i-propyl group, a n-butyl group, a s-butyl group, an i-butyl group, a t-butyl group, a n-pentyl group, and a n-hexyl group;

a C2-6 alkenyl group such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

a C2-6 alkynyl group such as an ethynyl group, a 1-propynyl group, a 2-propynyl group, a 1-butynyl group, a 2-butynyl group, a 3-butynyl group, and a 1-methyl-2-propynyl group;

a C3-8 cycloalkyl group such as a cyclopropyl group, a cyclobutyl group, a cyclopentyl group, a cyclohexyl group, and a cubanyl group;

a C6-10 aryl group such as a phenyl group and a naphthyl group;

a C6-10 aryl C1-6 alkyl group such as a benzyl group and a phenethyl group;

a 3- to 6-membered heterocyclyl group;

a 3- to 6-membered heterocyclyl C1-6 alkyl group;

a hydroxy group;

a C1-6 alkoxy group such as a methoxy group, an ethoxy group, a n-propoxy group, an i-propoxy group, a n-butoxy group, a s-butoxy group, an i-butoxy group, and a t-butoxy group;

a C2-6 alkenyloxy group such as a vinyloxy group, an allyloxy group, a propenyloxy group, and a butenyloxy group;

a C2-6 alkynyloxy group such as an ethynyloxy group and a propargyloxy group;

a C6-10 aryloxy group such as a phenoxy group and a naphthoxy group;

a C6-10 aryl C1-6 alkoxy group such as a benzyloxy group and a phenethyloxy group;

a 5- or 6-membered heteroaryloxy group such as a thiazolyloxy group and a pyridyloxy group;

a 5- or 6-membered heteroaryl C1-6 alkyloxy group such as a thiazolylmethyloxy group and a pyridylmethyloxy group;

a formyl group;

a C1-6 alkylcarbonyl group such as an acetyl group and a propionyl group;

a formyloxy group;

a C1-6 alkylcarbonyloxy group such as an acetyloxy group and a propionyloxy group;

a C6-10 arylcarbonyl group such as a benzoyl group;

a C1-6 alkoxycarbonyl group such as a methoxycarbonyl group, an ethoxycarbonyl group, a n-propoxycarbonyl group, an i-propoxycarbonyl group, a n-butoxycarbonyl group, and a t-butoxycarbonyl group;

a C1-6 alkoxycarbonyloxy group such as a methoxycarbonyloxy group, an ethoxycarbonyloxy group, a n-propoxycarbonyloxy group, an i-propoxycarbonyloxy group, a n-butoxycarbonyloxy group, and a t-butoxycarbonyloxy group;

a carboxy group;

a halogeno group such as a fluoro group, a chloro group, a bromo group, and an iodo group;

a C1-6 haloalkyl group such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group, and a 2,4,6-trichlorohexyl group;

a C2-6 haloalkenyl group such as a 2-chloro-1-propenyl group and a 2-fluoro-1-butenyl group;

a C2-6 haloalkynyl group such as a 4,4-dichloro-1-butynyl group, a 4-fluoro-1-pentynyl group, and a 5-bromo-2-pentynyl group;

a C1-6 haloalkoxy group such as a trifluoromethoxy group, a 2-chloro-n-propoxy group, a 2,3-dichlorobutoxy group, and a perfluoropropoxy group;

a C2-6 haloalkenyloxy group such as a 2-chloropropenyloxy group and a 3-bromobutenyloxy group;

a C1-6 haloalkylcarbonyl group such as a chloroacetyl group, a trifluoroacetyl group, and a trichloroacetyl group;

an amino group;

a C1-6 alkyl-substituted amino group such as a methylamino group, a dimethylamino group, and a diethylamino group;

a C6-10 arylamino group such as an anilino group and a naphthylamino group;

a C6-10 aryl C1-6 alkylamino group such as a benzylamino group and a phenethylamino group;

a formylamino group;

a C1-6 alkylcarbonylamino group such as an acetylamino group, a propanoylamino group, a butyrylamino group, and an i-propylcarbonylamino group;

a C1-6 alkoxycarbonylamino group such as a methoxycarbonylamino group, an ethoxycarbonylamino group, a n-propoxycarbonylamino group, and an i-propoxycarbonylamino group;

an unsubstituted or substituted aminocarbonyl group such as an aminocarbonyl group, a dimethylaminocarbonyl group, a phenylaminocarbonyl group, and a N-phenyl-N-methylaminocarbonyl group;

an imino C1-6 alkyl group such as an iminomethyl group, a (1-imino)ethyl group, and a (1-imino)-n-propyl group;

a substituted or unsubstituted N-hydroxyimino C1-6 alkyl group such as a N-hydroxy-iminomethyl group, a (1-(N-hydroxy)-imino)ethyl group, a (1-(N-hydroxy)-imino)propyl group, a N-methoxy-iminomethyl group, and a (1-(N-methoxy)-imino)ethyl group;

a C1-6 alkoxyimino group such as a methoxyimino group, an ethoxyimino group, a n-propoxyimino group, an i-propoxyimino group, and a n-butoxyimino group;

an aminocarbonyloxy group;

a C1-6 alkyl-substituted aminocarbonyloxy group such as an ethylaminocarbonyloxy group and a dimethylaminocarbonyloxy group;

a mercapto group;

a C1-6 alkylthio group such as a methylthio group, an ethylthio group, a n-propylthio group, an i-propylthio group, a n-butylthio group, an i-butylthio group, a s-butylthio group, and a t-butylthio group;

a C1-6 haloalkylthio group such as a trifluoromethylthio group and a 2,2,2-trifluoroethylthio group;

a C6-10 arylthio group such as a phenylthio group and a naphthylthio group;

a 5- or 6-membered heteroarylthio group such as a thiazolylthio group and a pyridylthio group;

a C1-6 alkylsulfinyl group such as a methylsulfinyl group, an ethylsulfinyl group, and a t-butylsulfinyl group;

a C1-6 haloalkylsulfinyl group such as a trifluoromethylsulfinyl group and a 2,2,2-trifluoroethylsulfinyl group;

a C6-10 arylsulfinyl group such as a phenylsulfinyl group;

a 5- or 6-membered heteroarylsulfinyl group such as a thiazolylsulfinyl group and a pyridylsulfinyl group;

a C1-6 alkylsulfonyl group such as a methylsulfonyl group, an ethylsulfonyl group, and a t-butylsulfonyl group;

a C1-6 haloalkylsulfonyl group such as a trifluoromethylsulfonyl group and a 2,2,2-trifluoroethylsulfonyl group;

a C6-10 arylsulfonyl group such as a phenylsulfonyl group;

a 5- or 6-membered heteroarylsulfonyl group such as a thiazolylsulfonyl group and a pyridylsulfonyl group;

a C1-6 alkylsulfonyloxy group such as a methylsulfonyloxy group, an ethylsulfonyloxy group, and a t-butylsulfonyloxy group;

a C1-6 haloalkylsulfonyloxy group such as a trifluoromethylsulfonyloxy group and a 2,2,2-trifluoroethylsulfonyloxy group;

and an aminothiocarbonyl group;

a tri-C1-6 alkyl-substituted silyl group such as a trimethylsilyl group, a triethylsilyl group, and a t-butyldimethylsilyl group;

a tri-C6-10 aryl-substituted silyl group such as a triphenylsilyl group;

a cyano group; and a nitro group.

For these "substituents", any hydrogen atom in each substituent may be substituted with a group having a distinct structure. In this case, as the "substituent", a C1-6 alkyl group, a C1-6 haloalkyl group, a C1-6 alkoxy group, a C1-6 haloalkoxy group, a halogeno group, a cyano group, a nitro group or the like may be exemplified.

The "3- to 6-membered heterocyclyl group" described above contains 1 to 4 heteroatoms selected from the group consisting of a nitrogen atom, an oxygen atom and a sulfur atom as ring-constituting atoms. The heterocyclyl group may be either monocyclic or polycyclic. The polycyclic heterocyclyl group has at least one hetero ring, and the remaining ring(s) may be any of a saturated alicyclic ring, an unsaturated alicyclic ring and an aromatic ring. As the "3- to 6-membered heterocyclyl group", a 3- to 6-membered saturated heterocyclyl group, a 5- or 6-membered heteroaryl group, a 5- or 6-membered partially unsaturated heterocyclyl group or the like may be exemplified.

As the 3- to 6-membered saturated heterocyclyl group, an aziridinyl group, an epoxy group, a pyrrolidinyl group, a tetrahydrofuranyl group, a thiazolidinyl group, a piperidyl group, a piperazinyl group, a morpholinyl group, a dioxolanyl group, a dioxanyl group or the like may be exemplified.

As the 5-membered heteroaryl group, a pyrrolyl group, a furyl group, a thienyl group, an imidazolyl group, a pyrazolyl group, an oxazolyl group, an isoxazolyl group, a triazolyl group, an isothiazolyl group, a triazolyl group, an oxadiazolyl group, a thiadiazolyl group, a tetrazolyl group or the like may be exemplified.

As the 6-membered heteroaryl group, a pyridyl group, a pyrazinyl group, a pyrimidinyl group, a pyridazinyl group, a triazinyl group or the like may be exemplified.

[$B^1$]

In the formula (I), $B^1$ represents a nitrogen atom or CH.

Specifically, the compound represented by the formula (I) is a compound represented by the following formula (I-1) or formula (I-2).

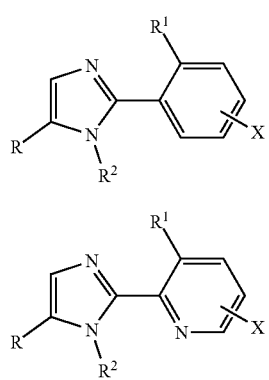

In the formula (I-1) and the formula (I-2), X, $R^1$, $R^2$ and R have the same meanings as described in the formula (I).

$B^1$ is preferably a nitrogen atom.

[X]

In the formula (I), X represents a substituted or unsubstituted C3-8 cycloalkyl group.

As the "C3-8 cycloalkyl group" in X, a cyclopropyl group, a cyclobutyl group, a cyclopentyl group, a cyclohexyl group, a cubanyl group or the like may be exemplified.

As the "substituted C3-8 cycloalkyl group" in X, a 1-methylcyclopropyl group, a 1-cyanocyclopropyl group, a 1-aminocarbonylcyclopropyl group, a 1-aminothiocarbonylcyclopropyl group, a 1-(pyridin-2-yl)cyclopropyl group or the like may be exemplified.

As the substituent on the "C3-8 cycloalkyl group" in X, a cyano group; an aminocarbonyl group; an aminothiocarbonyl group; a C1-6 alkyl group such as a methyl group, an ethyl group, a n-propyl group, an i-propyl group, a n-butyl group, a s-butyl group, an i-butyl group, a t-butyl group, a n-pentyl group, and a n-hexyl group; and a 6-membered heteroaryl group such as a pyridyl group, a pyrazinyl group, a pyrimidinyl group, a pyridazinyl group, and a triazinyl group may be preferably exemplified.

X is preferably a substituted or unsubstituted cyclopropyl group, and more preferably an unsubstituted cyclopropyl group.

[$R^1$]

In the formula (I), $R^1$ represents a substituted or unsubstituted C1-6 alkylthio group or a substituted or unsubstituted C1-6 alkylsulfonyl group.

As the "C1-6 alkylthio group" in $R^1$, a methylthio group, an ethylthio group, a n-propylthio group, an i-propylthio group, a n-butylthio group, an i-butylthio group, a s-butylthio group, a t-butylthio group or the like may be exemplified.

As the "C1-6 alkylsulfonyl group" in $R^1$, a methylsulfonyl group, an ethylsulfonyl group, a t-butylsulfonyl group or the like may be exemplified.

As the substituents on the "C1-6 alkylthio group" and the "C1-6 alkylsulfonyl group" in $R^1$, a halogeno group such as a fluoro group, a chloro group, a bromo group, and an iodo group may be preferably exemplified.

$R^1$ is preferably a C1-6 alkylsulfonyl group, and more preferably an ethylsulfonyl group.

[$R^2$]

In the formula (I), $R^2$ represents a substituted or unsubstituted C1-6 alkyl group.

The "C1-6 alkyl group" in $R^2$ may be linear or branched. As the "C1-6 alkyl group", a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, an i-hexyl group or the like may be exemplified.

As the substituent on the "C1-6 alkyl group" in $R^2$, a halogeno group such as a fluoro group, a chloro group, a bromo group, and an iodo group may be preferably exemplified.

$R^2$ is preferably an unsubstituted C1-6 alkyl group, and more preferably a methyl group.

[R]

In the formula (I), R represents a substituted or unsubstituted C2-6 alkenyl group.

As the "C2-6 alkenyl group" in R, a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group or the like may be exemplified.

As the "substituted C2-6 alkenyl group" in R, a C2-6 haloalkenyl group such as a 2-fluoro-2-bromovinyl group, a 2,2-dichlorovinyl group, a 2-chloro-2-iodovinyl group, a 2-chloro-1-propenyl group, a 2,3,3,3-tetrafluoro-1-propenyl group, a 3,3,3-trifluoro-1-propenyl group, a 2-chloro-3,3,3-trifluoro-1-propenyl group, a 2-bromo-3,3,3-trifluoro-1-propenyl group, a 3,3,3-trifluoro-2-trifluoromethyl-1-propenyl group, a 2-fluoro-1-butenyl group, a 3,3,4,4,4-pentafluoro-1-butenyl group, a 2,3,3,4,4,4-hexafluoro-1-butenyl group, a 2-chloro-3,3,4,4,4-pentafluoro-1-butenyl group, a 3,3,4,4,5,5,5-heptafluoro-1-pentenyl group, a 2-chloro-3,3,4,4,5,5,5-heptafluoro-1-pentenyl group, a 2,3,3,4,4,5,5,5-octafluoro-1-pentenyl group, and a 3,3,4,4,5,5,6,6,6-nonafluoro-1-hexenyl group; and a C1-6 haloalkoxy C2-6 haloalkenyl group such as a 1,2-difluoro-2-trifluoromethoxyvinyl group and a 1,2-difluoro-2-perfluoropropoxyvinyl group may be exemplified.

As the substituent on the "C2-6 alkenyl group" in R, a halogeno group such as a fluoro group, a chloro group, a bromo group, and an iodo group; and a C1-6 haloalkoxy group such as a trifluoromethoxy group, a 2-chloro-n-propoxy group, a 2,3-dichlorobutoxy group, and a perfluoropropoxy group may be preferably exemplified.

R is preferably a C2-6 haloalkenyl group.

The salt of the compound (I) is not particularly limited as long as the salt is agriculturally or horticulturally acceptable. As the salt of the compound (I), for example, a salt of an inorganic acid such as hydrochloric acid and sulfuric acid; a salt of an organic acid such as acetic acid and lactic acid; a salt of an alkali metal such as lithium, sodium and potassium; a salt of an alkaline earth metal such as calcium and magnesium; a salt of a transition metal such as iron and copper; a salt of an organic base such as ammonia, triethylamine, tributylamine, pyridine, and hydrazine, or the like may be exemplified.

[Compound Represented by Formula (II)]

The compound represented by the formula (I) is preferably a compound represented by the formula (II).

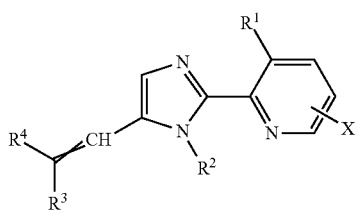

(II)

In the formula (II), $R^1$, $R^2$, and X have the same meanings as described in the formula (I).

$R^3$ represents a hydrogen atom or a halogeno group.

$R^4$ represents a C1-4 haloalkyl group.

In the formula (II), the carbon-carbon double stereo bond represents an E form or a Z form, or a mixture thereof.

[$R^3$]

As the "halogeno group" in $R^3$, a fluoro group, a chloro group, a bromo group, an iodo group or the like may be exemplified.

[$R^4$]

As the "C1-4 haloalkyl group" in $R^4$, a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group or the like may be exemplified.

$R^4$ is preferably a C1-4 fluoroalkyl group such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, or a perfluorobutyl group.

The compound represented by the formula (I) is preferably any of the following compounds.

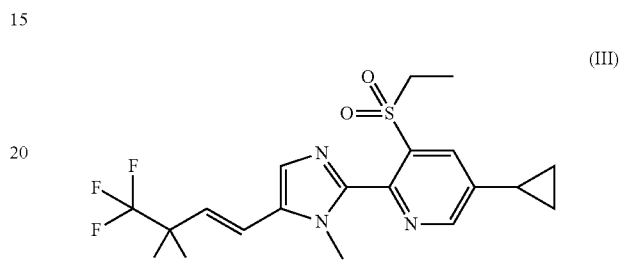

(III)

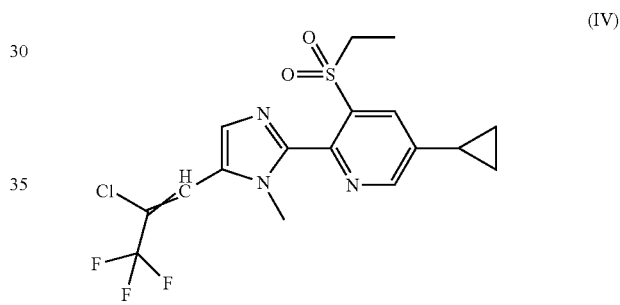

(IV)

wherein the carbon-carbon double stereo bond represents an E form or a Z form, or a mixture thereof.

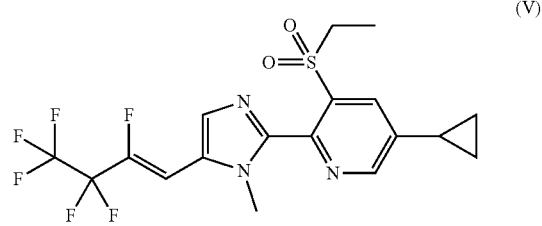

(V)

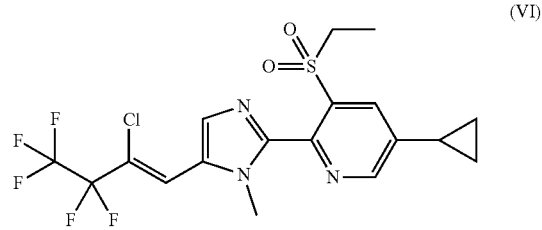

(VI)

(VII)

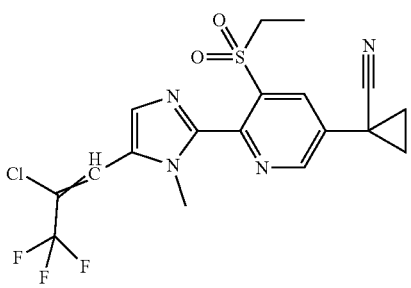

wherein the carbon-carbon double stereo bond represents an E form or a Z form, or a mixture thereof.

(VIII)

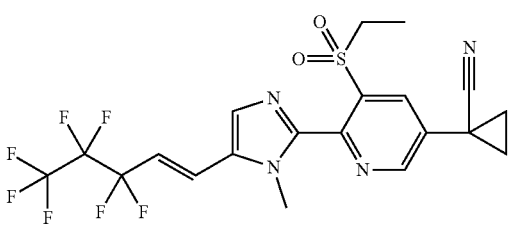

(IX)

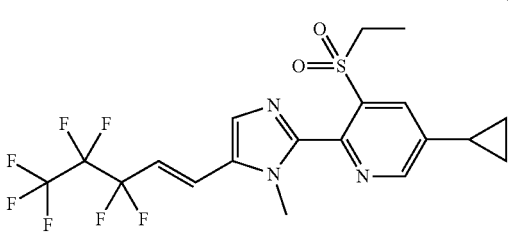

(X)

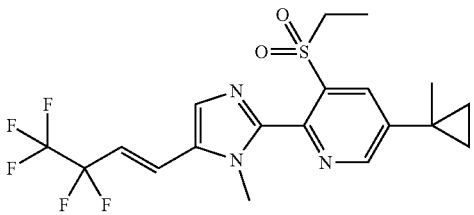

[Production Method]

The (hetero)aryl imidazole compound of the present invention is not particularly limited by its production method. For example, the (hetero)aryl imidazole compound of the present invention may be obtained by known production methods described in Examples, etc. Alternatively, the N-oxide compound, salt, or the like of the compound (I) may be obtained by a known approach from the compound (I).

The (hetero)aryl imidazole compound of the present invention may be produced by, for example, methods given below.

(Synthetic Method 1)

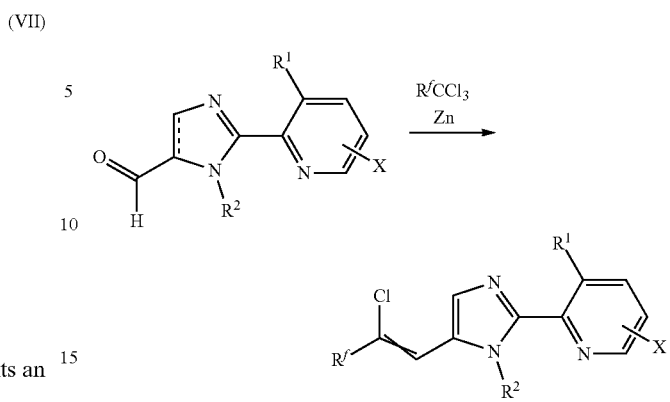

wherein X, $R^1$ and $R^2$ have the same meanings as described above; and $R_f$ represents a C1-4 fluoroalkyl group such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, or a perfluorobutyl group.

(Synthetic Method 2)

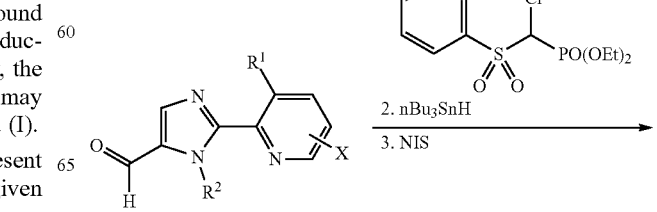

wherein X, $R^1$, $R^2$ and $R^f$ have the same meanings as described above; and $R^5$ represents a C1-6 alkyl group.

(Synthetic Method 3)

-continued

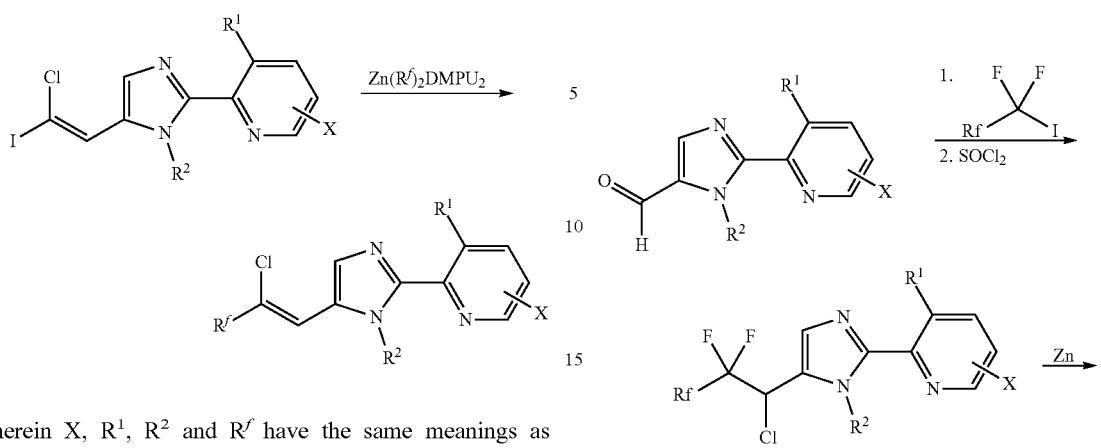

wherein X, R¹, R² and R^f have the same meanings as described above.

(Synthetic Method 4)

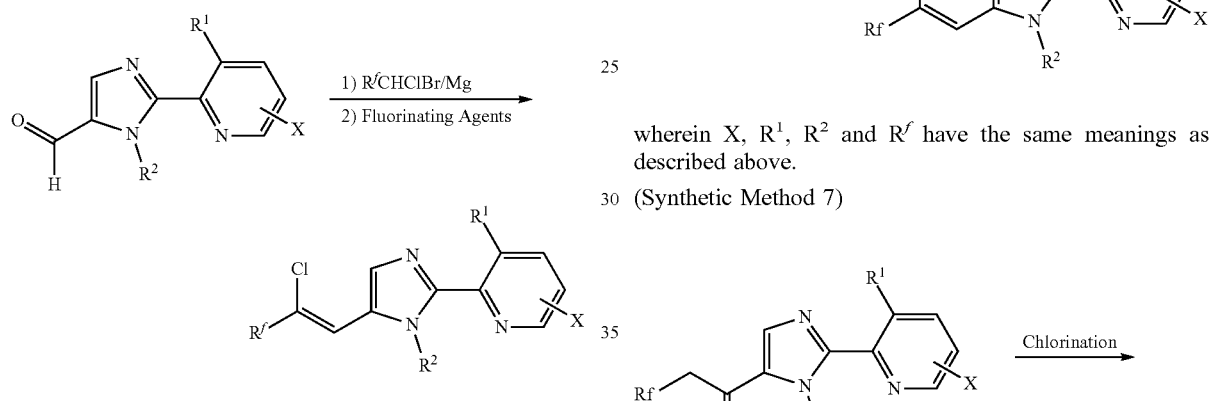

wherein X, R¹, R² and R^f have the same meanings as described above.

(Synthetic Method 5)

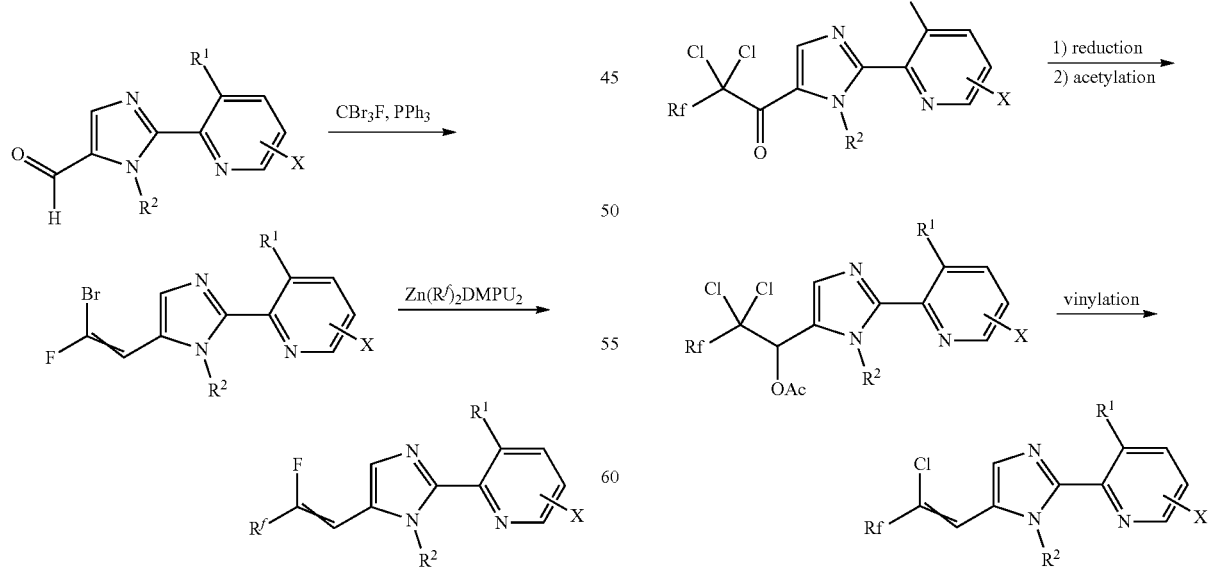

wherein X, R¹, R² and R^f have the same meanings as described above.

(Synthetic Method 6)

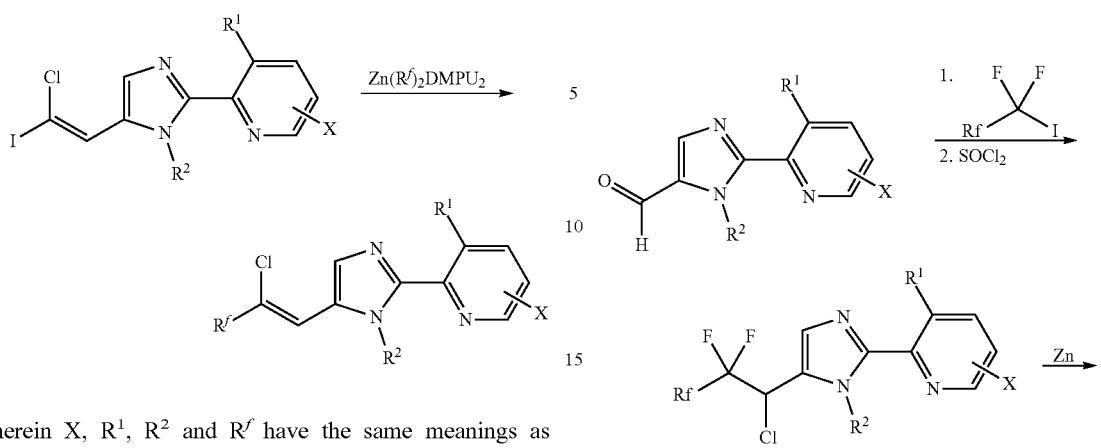

wherein X, R¹, R² and R^f have the same meanings as described above.

(Synthetic Method 7)

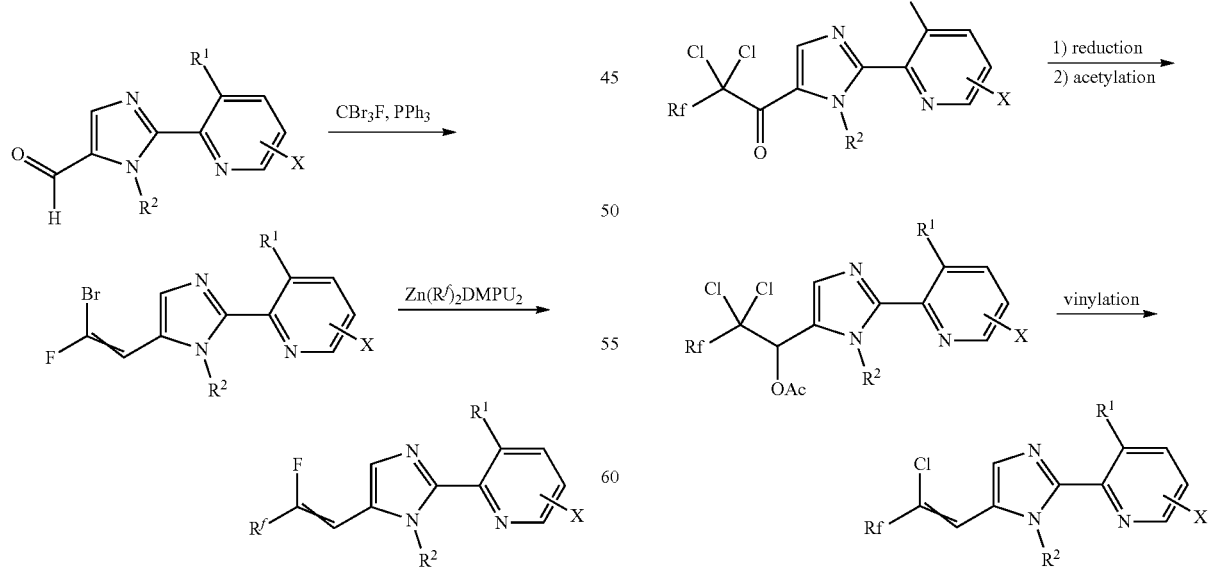

wherein X, R¹, R² and R^f have the same meanings as described above.

(Synthetic Method 8)

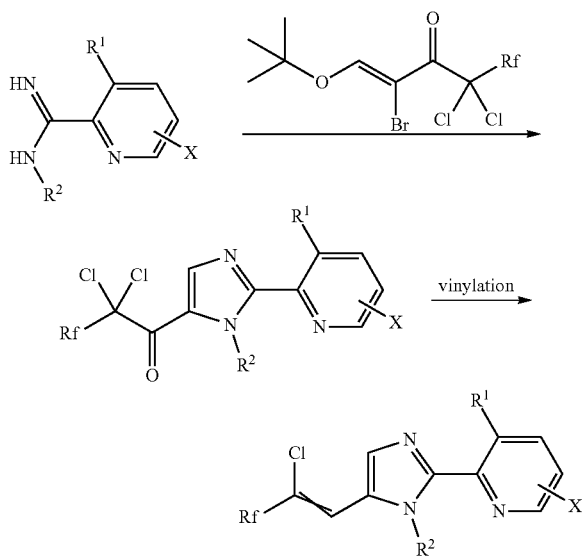

wherein X, $R^1$, $R^2$ and $R^f$ have the same meanings as described above.

(Synthetic Method 9)

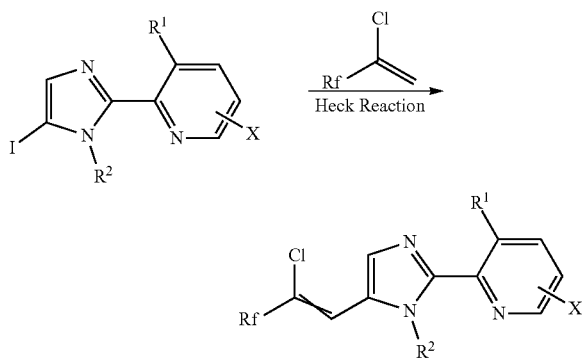

wherein X, $R^1$, $R^2$ and $R^f$ have the same meanings as described above.

[Control Effect on Pest]

The (hetero)aryl imidazole compound of the present invention is excellent in control effect on pests such as various agricultural insect pests and acari affecting the growth of plants.

Also, the (hetero)aryl imidazole compound of the present invention is a highly safe substance because of less phytotoxicity to crops and low toxicity to fishes and warm-blooded animals. Hence, the (hetero)aryl imidazole compound of the present invention is useful as an active ingredient for insecticides or acaricides.

Furthermore, in recent years, many insect pests such as diamondback moth, white-backed plant hopper, leafhopper, and aphid have developed resistance to various existing chemicals, causing problems of insufficient efficacy of these chemicals. Thus, chemicals effective for insect pests of resistant strains have been desired. The (hetero)aryl imidazole compound of the present invention exhibits an excellent control effect not only on sensitive strains but also on insect pests of various resistant strains and even acari of acaricide-resistant strains.

The (hetero)aryl imidazole compound of the present invention is excellent in control effect on ectoparasites and endoparasites harmful to humans and animals. Also, the (hetero)aryl imidazole compound of the present invention is a highly safe substance because of low toxicity to fishes and warm-blooded animals. Hence, the (hetero)aryl imidazole compound of the present invention is useful as an active ingredient for ectoparasite and endoparasite control agents.

The (hetero)aryl imidazole compound of the present invention exhibits efficacy at every developmental stage of organisms to be controlled, and exhibits an excellent control effect on, for example, eggs, nymphs, larvae, pupae, and adults of acari, insects, and the like.

[Pest Control Agent]

The pest control agent of the present invention contains at least one active ingredient selected from the (hetero)aryl imidazole compounds of the present invention. The amount of the (hetero)aryl imidazole compound contained in the pest control agent of the present invention is not particularly limited as long as its pest control effect is exhibited. The pest control agent is an agent controlling pests and includes an insecticide or acaricide, an ectoparasite control agent, or an endoparasite control agent or expellant, or the like.

The pest control agent of the present invention may be used as a mixture or in combination with another active ingredient such as a fungicide, an insecticide or acaricide, a nematicide, or a pesticide for soil insect pests; a plant regulating agent, a synergist, a fertilizer, a soil improvement agent, animal feed, or the like.

The combination of the (hetero)aryl imidazole compound of the present invention with another active ingredient may be expected to have synergistic effects on insecticidal, acaricidal, or nematicidal activity. The synergistic effects may be confirmed by the equation of Colby (Colby. S. R.; Calculating Synergistic and Antagonistic Responses of Herbicide Combinations; Weeds 15, p. 20-22, 1967) according to a standard method.

Specific examples of the insecticide or acaricide, the nematicide, the pesticide for soil insect pests, the anthelmintic agent, and the like that may be used as a mixture or in combination with the pest control agent of the present invention will be shown below.

(1) Acetylcholinesterase inhibitors:
(a) carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, chloethocarb, metam sodium, and promecarb;
(b) organophosphorus-based: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion, bromophos-ethyl, BRP, carbophenothion, cyanofenphos, CYAP, demeton-S-methyl sulfone, dialifos, dichlofenthion, dioxabenzofos, etrimfos, fensulfothion, flupyrazofos, fonofos, formothion, fosmethilan, isazofos, iodofenphos, methacrifos, pirimiphos-ethyl, phosphocarb, propaphos, prothoate, and sulprofos.

(2) GABAergic chloride ion channel antagonists: acetoprole, chlordene, endosulfan, ethiprole, fipronil, pyrafluprole, pyriprole, camphechlor, heptachlor, and dienochlor.

(3) Sodium channel modulators: acrinathrin, d-cis-trans allethrin, d-trans allethrin, bifenthrin, bioallethrin, bioallethrin S-cyclopentyl isomers, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomers], prallethrin, pyrethrum, resmethrin, silafluofen, tefluthrin, tetramethrin [(1R)-isomers], tralomethrin, transfluthrin, allethrin, pyrethrin, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, and terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, flupyradifurone, and flupyrimin.

(5) Nicotinic acetylcholine receptor allosteric modulators: spinetoram and spinosad.

(6) Chloride channel activators: abamectin, emamectin benzoate, lepimectin, milbemectin, ivermectin, selamectin, doramectin, eprinomectin, moxidectin, milbemycin, milbemycin oxime, and nemadectin.

(7) Juvenile hormone-like substances: hydroprene, kinoprene, methoprene, fenoxycarb, pyriproxyfen, diofenolan, epofenonane, and triprene.

(8) Other nonspecific inhibitors: methyl bromide, chloropicrin, sulfuryl fluoride, borax, and tartar emetic.

(9) Homoptera selective feeding inhibitors: flonicamid, pymetrozine, and pyrifluquinazon.

(10) Mite growth inhibitors: clofentezine, diflovidazin, hexythiazox, and etoxazole.

(11) Insect midgut inner membrane disrupting agents derived from microorganisms: Bacillus thuringiensis subsp. Isuraerenshi, Bacillus sphaericus, Bacillus thuringiensis subsp. Aizawai, Bacillus thuringiensis subsp. Kurstaki, Bacillus thuringiensis subsp. Tenebrionis, and Bt crop proteins: Cry1Ab, Cry1Ac, Cry1Fa, Cry1A.105, Cry2Ab, Vip3A, mCry3A, Cry3Ab, Cry3Bb, and Cry34Ab1/Cry35Ab1.

(12) Mitochondrial ATP biosynthetic enzyme inhibitors: diafenthiuron, azocyclotin, cyhexatin, fenbutatin oxide, propargite, and tetradifon.

(13) Oxidative phosphorylation uncouplers: chlorfenapyr, sulfluramid, DNOC, binapacryl, dinobuton, and dinocap.

(14) Nicotinic acetylcholine receptor channel blockers: bensultap, cartap hydrochloride, nereistoxin, thiosultap sodium, and thiocyclam.

(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, and fluazuron.

(16) Diptera molting disrupting agents: cyromazine.

(17) Molting hormone receptor agonists: chromafenozide, halofenozide, methoxyfenozide, and tebufenozide.

(18) Octopamine receptor agonists: amitraz, demiditraz, and chlordimeform.

(19) Mitochondrial electron transport system complex III inhibitors: acequinocyl, fluacrypyrim, and hydramethylnon.

(20) Mitochondrial electron transport system complex I inhibitors: fenazaquin, fenpyroximate, pyrimidifen, pyridaben, tebufenpyrad, tolfenpyrad, and rotenone.

(21) Voltage-gated sodium channel blockers: indoxacarb and metaflumizone.

(22) Acetyl CoA carboxylase inhibitors: spirodiclofen, spiromesifen, and spirotetramat.

(23) Mitochondrial electron transport system complex IV inhibitors: aluminum phosphide, calcium phosphide, phosphine, zinc phosphide, and cyanide.

(24) Mitochondrial electron transport system complex II inhibitors: cyenopyrafen, cyflumetofen, and pyflubumide.

(25) Ryanodine receptor modulators: chlorantraniliprole, cyantraniliprole, flubendiamide, cyclaniliprole, and tetraniliprole.

(26) Mixed function oxidase inhibitor compounds: piperonyl butoxide.

(27) Latrophilin receptor agonists: depsipeptide, cyclic depsipeptide, 24-membered cyclic depsipeptide, and emodepside.

(28) Other agents (based on an unknown mechanism of action): azadirachtin, benzoximate, bifenazate, bromopropylate, chinomethionate, cryolite, dicofol, pyridalyl, benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimin, fluphenazine, gossyplure, japonilure, metoxadiazone, petroleum, potassium oleate, tetrasul, triarathene, afidopyropen, flometoquin, flufiprole, fluensulfone, meperfluthrin, tetramethylfluthrin, tralopyril, dimefluthrin, methylneodecanamide, fluralaner, afoxolaner, fluxametamide, 5-[5-(3,5-dichlorophenyl)-5-trifluoromethyl-4,5-dihydroisoxazol-3-yl]-2-(1H-1,2,4-triazol-1-yl)benzonitrile (CAS: 943137-49-3), broflanilide, and other m-diamides.

(29) Anthelmintic agents:
  (a) benzimidazole-based: fenbendazole, albendazole, triclabendazole, oxibendazole, mebendazole, oxfendazole, parbendazole, flubendazole, febantel, netobimin, thiophanate, thiabendazole, and cambendazole;
  (b) salicylanilide-based: closantel, oxyclozanide, rafoxanide, and niclosamide;
  (c) substituted phenol-based: nitroxinil and nitroscanate;
  (d) pyrimidine-based: pyrantel and morantel;
  (e) imidazothiazole-based: levamisole and tetramisole;
  (f) tetrahydropyrimidine-based: praziquantel and epsiprantel;
  (g) other anthelmintic agents: cyclodiene, ryania, clorsulon, metronidazole, demiditraz, piperazine, diethylcarbamazine, dichlorophene, monepantel, tribendimidine, amidantel, thiacetarsamide, melarsomine, and arsenamide.

Specific examples of the fungicide that may be used as a mixture or in combination with the pest control agent of the present invention will be shown below.

(1) Nucleic acid biosynthesis inhibitors:
  (a) RNA polymerase I inhibitors: benalaxyl, benalaxyl-M, furalaxyl, metalaxyl, metalaxyl-M, oxadixyl, clozylacon, and ofurace;
  (b) adenosine deaminase inhibitors: bupirimate, dimethirimol, and ethirimol;

(c) DNA/RNA synthesis inhibitors: hymexazol and octhilinone;
(d) DNA topoisomerase II inhibitors: oxolinic acid.
(2) Mitotic inhibitors and cell division inhibitors:
  (a) β-tubulin polymerization inhibitors: benomyl, carbendazim, chlorfenazole, fuberidazole, thiabendazole, thiophanate, thiophanate-methyl, diethofencarb, zoxamide, and ethaboxam;
  (b) cell division inhibitors: pencycuron;
  (c) spectrin-like protein delocalization inhibitors: fluopicolide.
(3) Respiration inhibitors:
  (a) complex I NADH oxidation-reduction enzyme inhibitors: diflumetorim and tolfenpyrad;
  (b) complex II succinate dehydrogenase inhibitors: benodanil, flutolanil, mepronil, isofetamid, fluopyram, fenfuram, furmecyclox, carboxin, oxycarboxin, thifluzamide, benzovindiflupyr, bixafen, fluxapyroxad, furametpyr, isopyrazam, penflufen, penthiopyrad, sedaxane, and boscalid;
  (c) complex III ubiquinol oxidase Qo inhibitors: azoxystrobin, coumoxystrobin, coumethoxystrobin, enoxastrobin, flufenoxystrobin, picoxystrobin, pyraoxystrobin, pyraclostrobin, pyrametostrobin, triclopyricarb, kresoxim-methyl, trifloxystrobin, dimoxystrobin, fenaminstrobin, metominostrobin, orysastrobin, famoxadone, fluoxastrobin, fenamidone, and pyribencarb;
  (d) complex III ubiquinol reductase Qi inhibitors: cyazofamid and amisulbrom;
  (e) oxidative phosphorylation uncoupling agents: binapacryl, meptyldinocap, dinocap, fluazinam, and ferimzone;
  (f) oxidative phosphorylation inhibitors (ATP synthase inhibitors): fentin acetate, fentin chloride, and fentin hydroxide;
  (g) ATP production inhibitors: silthiofam;
  (h) complex III: Qx (unknown) inhibitor of cytochrome bc1 (ubiquinone reductase): ametoctradin.
(4) Amino acid and protein synthesis inhibitors
  (a) methionine biosynthesis inhibitors: andoprim, cyprodinil, mepanipyrim, and pyrimethanil;
  (b) protein synthesis inhibitors: blasticidin-S, kasugamycin, kasugamycin hydrochloride, streptomycin, and oxytetracycline.
(5) Signal transduction inhibitors:
  (a) signal transduction inhibitors: quinoxyfen and proquinazid;
  (b) MAP/histidine kinase inhibitors in osmotic signal transduction: fenpiclonil, fludioxonil, chlozolinate, iprodione, procymidone, and vinclozolin.
(6) Lipid and cell membrane synthesis inhibitors:
  (a) phospholipid biosynthesis, methyltransferase inhibitors: edifenphos, iprobenfos, pyrazophos, and isoprothiolane;
  (b) lipid peroxidation agents: biphenyl, chloroneb, dicloran, quintozene, tecnazene, tolclofos-methyl, and etridiazole;
  (c) agents that act on cell membranes: iodocarb, propamocarb, propamocarb hydrochloride, propamocarb fosetylate, and prothiocarb;
  (d) microorganisms that disrupt cell membranes of pathogens: *Bacillus subtilis* bacteria, *Bacillus subtilis* QST713 strain, *Bacillus subtilis* FZB24 strain, *Bacillus subtilis* MBI600 strain, and *Bacillus subtilis* D747 strain;
  (e) agents that disrupt cell membranes: extracts of *Melaleuca alternifolia* (tea tree).
(7) Cell membrane sterol biosynthesis inhibitors:
  (a) C14-demethylation inhibitors in sterol biosynthesis: triforine, pyrifenox, pyrisoxazole, fenarimol, flurprimidol, nuarimol, imazalil, imazalil sulfate, oxpoconazole, pefurazoate, prochloraz, triflumizole, viniconazole, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, fluconazole, fluconazole-cis, hexaconazole, imibenconazole, ipconazole, metconazole, myclobutanil, penconazole, propiconazole, quinconazole, simeconazole, tebuconazole, tetraconazole, triadimefon, triadimenol, triticonazole, prothioconazole, and voriconazole;
  (b) Δ14 reductase and sterol Δ8→Δ7-isomerase inhibitors in sterol biosynthesis: aldimorph, dodemorph, dodemorph acetate, fenpropimorph, tridemorph, fenpropidin, piperalin, and spiroxamine;
  (c) 3-keto reductase inhibitors in C4-demethylation in the sterol biosynthesis system: fenhexamid and fenpyrazamine;
  (d) squalene epoxidase inhibitors in the sterol biosynthesis system: pyributicarb, naftifine, and terbinafine.
(8) Cell wall synthesis inhibitors
  (a) trehalase inhibitors: validamycin;
  (b) chitin synthase inhibitors: polyoxin and polyoxorim;
  (c) cellulose synthase inhibitors: dimethomorph, flumorph, pyrimorph, benthiavalicarb, iprovalicarb, tolprocarb, valifenalate, and mandipropamid.
(9) Melanin biosynthesis inhibitors
  (a) melanin biosynthesis reductase inhibitors: fthalide, pyroquilon, and tricyclazole;
  (b) melanin biosynthesis anhydrase inhibitors: carpropamid, diclocymet, and fenoxanil;
(10) Host plant resistance inducers:
  (a) agents that act on salicylic acid synthesis pathway: acibenzolar-S-methyl;
  (b) others: probenazole, tiadinil, isotianil, laminarin, and giant knotweed extracts.
(11) Agents with unknown mode of action: cymoxanil, fosetyl aluminum, phosphoric acid (phosphate), tecloftalam, triazoxide, flusulfamide, diclomezine, methasulfocarb, cyflufenamid, metrafenone, pyriofenone, dodine, dodine free base, and flutianil.
(12) Agents having multiple active sites: copper (copper salt), Bordeaux mixture, copper hydroxide, copper naphthalate, copper oxide, copper oxychloride, copper sulfate, sulfur, sulfur products, calcium polysulfide, ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine triacetate, iminoctadine trialbesilate, anilazine, dithianon, chinomethionate, and fluoroimide.
(13) Other agents: DBEDC, fluoro folpet, guazatine acetate, bis(8-quinolinolato)copper(II), propamidine, chloropicrin, cyprofuram, agrobacterium, bethoxazin, diphenylamine, methyl isothiocyanate (MITC), mildiomycin, capsaicin, cufraneb, cyprosulfamide, dazomet, debacarb, dichlorophene, difenzoquat, difenzoquat methyl sulfonate, flumetover, fosetyl calcium, fosetyl sodium, irumamycin, natamycin, nitrothal-isopropyl, oxamocarb, propanosine sodium, pyrrolnitrin, tebufloquin, tolnifanide, zarilamid, algophase, amicarthiazol, oxathiapiprolin, metiram zinc, benthiazole, trichlamide, uniconazole, oxyfenthiin, and picarbutrazox.

Specific examples of the plant regulating agent that may be used as a mixture or in combination with the pest control agent of the present invention will be shown below.

Abscisic acid, kinetin, benzylaminopurine, 1,3-diphenylurea, forchlorfenuron, thidiazuron, chlorfenuron, dihydrozeatin, gibberellin A, gibberellin A4, gibberellin A7, gibberellin A3, 1-methylcyclopropane, N-acetylaminoethoxyvinylglycine (also called aviglycine), aminooxyacetic acid, silver nitrate, cobalt chloride, IAA, 4-CPA, cloprop, 2,4-D, MCPB, indole-3-butyric acid, dichlorprop, phenothiol, 1-naphthyl acetamide, ethychlozate, cloxyfonac, maleic acid hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl)aminobutyric acid, ethephon, chlormequat, mepiquat chloride, benzyl adenine, and 5-aminolevulinic acid.

[Insecticide or Acaricide]

The insecticide or acaricide of the present invention contains at least one active ingredient selected from the (hetero)aryl imidazole compounds of the present invention. The amount of the (hetero)aryl imidazole compound contained in the insecticide or acaricide of the present invention is not particularly limited as long as its insecticidal or acaricidal effect is exhibited.

The insecticide or acaricide of the present invention is preferably used for plants such as cereals; vegetables; root vegetables; tubers and roots; flowers and ornamental plants; fruit trees; ornamental foliage plants and trees of tea, coffee, cacao, and the like; feed crops; lawn grasses; and cotton.

In the application to plants, the pest control agent or the insecticide or acaricide of the present invention may be used for any site such as a leaf, a stem, a stalk, a flower, a bud, a fruit, a seed, a sprout, a root, a tuber, a tuberous root, a shoot, or a slip.

The insecticide or acaricide of the present invention is not particularly limited by the species of the plant to which the pest control agent or the insecticide or acaricide is applied. As the plant species, for example, an original species, a variant species, an improved variety, a cultivar, a mutant, a hybrid, a genetically modified organism (GMO) or the like may be exemplified.

The insecticide or acaricide of the present invention may be used in seed treatment, foliage application, soil application, submerged application, or the like in order to control various agricultural insect pests and acari.

Specific examples of various agricultural insect pests and acari controllable with the insecticide or acaricide of the present invention will be shown below.

(1) Butterflies or Moths of the Order Lepidoptera
  (a) moths of the family Arctiidae, for example, *Hyphantria cunea* and *Lemyra imparilis*;
  (b) moths of the family Bucculatricidae, for example, *Bucculatrix pyrivorella*;
  (c) moths of the family Carposinidae, for example, *Carposina sasakii*;
  (d) moths of the family Crambidae, for example, *Diaphania indica* and *Diaphania nitidalis* of *Diaphania* spp.; for example, *Ostrinia furnacalis*, *Ostrinia nubilalis*, and *Ostrinia scapulalis* of *Ostrinia* spp.; and *Chilo suppressalis*, *Cnaphalocrocis medinalis*, *Conogethes punctiferalis*, *Diatraea grandiosella*, *Glyphodes pyloalis*, *Hellula undalis*, and *Parapediasia teterrella*;
  (e) moths of the family Gelechiidae, for example, *Helcystogramma triannulella*, *Pectinophora gossypiella*, *Phthorimaea operculella*, and *Sitotroga cerealella*;
  (f) moths of the family Geometridae, for example, *Ascotis selenaria*;
  (g) moths of the family Gracillariidae, for example, *Caloptilia theivora*, *Phyllocnistis citrella*, and *Phyllonorycter ringoniella*;
  (h) butterflies of the family Hesperiidae, for example, *Parnara guttata*;
  (i) moths of the family Lasiocampidae, for example, *Malacosoma neustria*;
  (j) moths of the family Lymantriidae, for example, *Lymantria dispar* and *Lymantria monacha* of *Lymantria* spp.; and *Euproctis pseudoconspersa* and *Orgyia thyellina*;
  (k) moths of the family Lyonetiidae, for example, *Lyonetia clerkella* and *Lyonetia prunifoliella malinella* of *Lyonetia* spp.;
  (l) moths of the family Noctuidae, for example, *Spodoptera depravata*, *Spodoptera eridania*, *Spodoptera exigua*, *Spodoptera frugiperda*, *Spodoptera littoralis*, and *Spodoptera litura* of *Spodoptera* spp.; for example, *Autographa gamma* and *Autographa nigrisigna* of *Autographa* spp.; for example, *Agrotis ipsilon* and *Agrotis segetum* of *Agrotis* spp.; for example, *Helicoverpa armigera*, *Helicoverpa assulta*, and *Helicoverpa zea* of *Helicoverpa* spp.; for example, *Heliothis armigera* and *Heliothis virescens* of *Heliothis* spp.; and *Aedia leucomelas*, *Ctenoplusia agnata*, *Eudocima tyrannus*, *Mamestra brassicae*, *Mythimna separata*, *Naranga aenescens*, *Panolis japonica*, *Peridroma saucia*, *Pseudoplusia includens*, and *Trichoplusia ni*;
  (m) moths of the family Nolidae, for example, *Earias insulana*;
  (n) butterflies of the family Pieridae, for example, *Pieris brassicae* and *Pieris rapae crucivora* of *Pieris* spp.;
  (o) moths of the family Plutellidae, for example, *Acrolepiopsis sapporensis* and *Acrolepiopsis suzukiella* of *Acrolepiopsis* spp.; and *Plutella xylostella*;
  (p) moths of the family Pyralidae, for example, *Cadra cautella*, *Elasmopalpus lignosellus*, *Etiella zinckenella*, and *Galleria mellonella*;
  (q) moths of the family Sphingidae, for example, *Manduca quinquemaculata* and *Manduca sexta* of *Manduca* spp.;
  (r) moths of the family Stathmopodidae, for example, *Stathmopoda masinissa*;
  (s) moths of the family Tineidae, for example, *Tinea translucens*;
  (t) moths of the family Tortricidae, for example, *Adoxophyes honmai* and *Adoxophyes orana* of *Adoxophyes* spp.; for example, *Archips breviplicanus* and *Archips fuscocupreanus* of *Archips* spp.; and *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana*, and *Sparganothis pilleriana*;
  (u) moths of the family Yponomeutidae, for example, *Argyresthia conjugella*.

(2) Insect Pests of the Order Thysanoptera
  (a) insect pests of the family Phlaeothripidae, for example, *Ponticulothrips diospyrosi*;
  (b) insect pests of the family Thripidae, for example, *Frankliniella intonsa* and *Frankliniella occidentalis* of *Frankliniella* spp.; for example, *Thrips palmi* and *Thrips tabaci* of *Thrips* spp.; and *Heliothrips haemorrhoidalis* and *Scirtothrips dorsalis*.

(3) Insect Pests of the Order Hemiptera
(A) the Suborder Archaeorrhyncha
- (a) insect pests of the family Delphacidae, for example, *Laodelphax striatella*, *Nilaparvata lugens*, *Perkinsiella saccharicida*, and *Sogatella furcifera*.

(B) The Suborder Clypeorrhyncha
- (a) insect pests of the family Cicadellidae, for example, *Empoasca fabae*, *Empoasca nipponica*, *Empoasca onukii*, and *Empoasca sakaii* of *Empoasca* spp.; and *Arboridia apicalis*, *Balclutha saltuella*, *Epiacanthus stramineus*, *Macrosteles striifrons*, and *Nephotettix cinctinceps*.

(C) The Suborder Heteroptera
- (a) insect pests of the family Alydidae, for example, *Riptortus clavatus*;
- (b) insect pests of the family Coreidae, for example, *Cletus punctiger* and *Leptocorisa chinensis*;
- (c) insect pests of the family Lygaeidae, for example, *Blissus leucopterus*, *Cavelerius saccharivorus*, and *Togo hemipterus*;
- (d) insect pests of the family Miridae, for example, *Halticus insularis*, *Lygus lineolaris*, *Psuedatomoscelis seriatus*, *Stenodema sibiricum*, *Stenotus rubrovittatus*, and *Trigonotylus caelestialium*;
- (e) insect pests of the family Pentatomidae, for example, *Nezara antennata* and *Nezara viridula* of *Nezara* spp.; for example, *Eysarcoris aeneus*, *Eysarcoris lewisi*, and *Eysarcoris ventralis* of *Eysarcoris* spp.; and *Dolycoris baccarum*, *Eurydema rugosum*, *Glaucias subpunctatus*, *Halyomorpha halys*, *Piezodorus hybneri*, *Plautia crossota*, and *Scotinophora lurida*;
- (f) insect pests of the family Pyrrhocoridae, for example, *Dysdercus cingulatus*;
- (g) insect pests of the family Rhopalidae, for example, *Rhopalus msculatus*;
- (h) insect pests of the family Scutelleridae, for example, *Eurygaster integriceps*;
- (i) insect pests of the family Tingidae, for example, *Stephanitis nashi*.

(D) The Suborder Sternorrhyncha
- (a) insect pests of the family Adelgidae, for example, *Adelges laricis*;
- (b) insect pests of the family Aleyrodidae, for example, *Bemisia argentifolii* and *Bemisia tabaci* of *Bemisia* spp.; and *Aleurocanthus spiniferus*, *Dialeurodes citri*, and *Trialeurodes vaporariorum*;
- (c) insect pests of the family Aphididae, for example, *Aphis craccivora*, *Aphis fabae*, *Aphis forbesi*, *Aphis gossypii*, *Aphis pomi*, *Aphis sambuci*, and *Aphis spiraecola* of *Aphis* spp.; for example, *Rhopalosiphum maidis* and *Rhopalosiphum padi* of *Rhopalosiphum* spp.; for example, *Dysaphis plantaginea* and *Dysaphis radicola* of *Dysaphis* spp.; for example, *Macrosiphum avenae* and *Macrosiphum euphorbiae* of *Macrosiphum* spp.; for example, *Myzus cerasi*, *Myzus persicae*, and *Myzus varians* of *Myzus* spp.; and *Acyrthosiphon pisum*, *Aulacorthum solani*, *Brachycaudus helichrysi*, *Brevicoryne brassicae*, *Chaetosiphon fragaefolii*, *Hyalopterus pruni*, *Hyperomyzus lactucae*, *Lipaphis erysimi*, *Megoura viciae*, *Metopolophium dirhodum*, *Nasonovia ribis-nigri*, *Phorodon humuli*, *Schizaphis graminum*, *Sitobion avenae*, and *Toxoptera aurantii*;
- (d) insect pests of the family Coccidae, for example, *Ceroplastes ceriferus* and *Ceroplastes rubens* of *Ceroplastes* spp.;
- (e) insect pests of the family Diaspididae, *Pseudaulacaspis pentagona* and *Pseudaulacaspis prunicola* of *Pseudaulacaspis* spp.; for example, *Unaspis euonymi* and *Unaspis yanonensis* of *Unaspis* spp.; and *Aonidiella aurantii*, *Comstockaspis perniciosa*, *Fiorinia theae*, and *Pseudaonidia paeoniae*;
- (f) insect pests of the family Margarodidae, for example, *Drosicha corpulenta* and *Icerya purchasi*;
- (g) insect pests of the family Phylloxeridae, for example, *Viteus vitifolii*;
- (h) insect pests of the family Pseudococcidae, for example, *Planococcus citri* and *Planococcus kuraunhiae* of *Planococcus* spp.; and *Phenacoccus solani* and *Pseudococcus comstocki*;
- (i) insect pests of the family Psyllidae, for example, *Psylla mali* and *Psylla pyrisuga* of *Psylla* spp.; and *Diaphorina citri*.

(4) Insect Pests of the Suborder Polyphaga
- (a) insect pests of the family Anobiidae, for example, *Lasioderma serricorne*;
- (b) insect pests of the family Attelabidae, for example, *Byctiscus betulae* and *Rhynchites heros*;
- (c) insect pests of the family Bostrichidae, for example, *Lyctus brunneus*;
- (d) insect pests of the family Brentidae, for example, *Cylas formicarius*;
- (e) insect pests of the family Buprestidae, for example, *Agrilus sinuatus*;
- (f) insect pests of the family Cerambycidae, for example, *Anoplophora malasiaca*, *Monochamus alternatus*, *Psacothea hilaris*, and *Xylotrechus pyrrhoderus*;
- (g) insect pests of the family Chrysomelidae, for example, *Bruchus pisorum* and *Bruchus rufimanus* of *Bruchus* spp.; for example, *Diabrotica barberi*, *Diabrotica undecimpunctata*, and *Diabrotica virgifera* of *Diabrotica* spp.; for example, *Phyllotreta nemorum* and *Phyllotreta striolata* of *Phyllotreta* spp.; and *Aulacophora femoralis*, *Callosobruchus chinensis*, *Cassida nebulosa*, *Chaetocnema concinna*, *Leptinotarsa decemlineata*, *Oulema oryzae*, and *Psylliodes angusticollis*;
- (h) insect pests of the family Coccinellidae, for example, *Epilachna varivestis* and *Epilachna vigintioctopunctata* of *Epilachna* spp.;
- (i) insect pests of the family Curculionidae, for example, *Anthonomus grandis* and *Anthonomus pomorum* of *Anthonomus* spp.; for example, *Sitophilus granarius* and *Sitophilus zeamais* of *Sitophilus* spp.; and *Echinocnemus squameus*, *Euscepes postfasciatus*, *Hylobius abietis*, *Hypera postica*, *Lissohoptrus oryzophilus*, *Otiorhynchus sulcatus*, *Sitona lineatus*, and *Sphenophorus venatus*;
- (j) insect pests of the family Elateridae, for example, *Melanotus fortnumi* and *Melanotus tamsuyensis* of *Melanotus* spp.;
- (k) insect pests of the family Nitidulidae, for example, *Epuraea domina*;
- (l) insect pests of the family Scarabaeidae, for example, *Anomala cuprea* and *Anomala rufocuprea* of *Anomala* spp.; and *Cetonia aurata*, *Gametis jucunda*, *Heptophylla picea*, *Melolontha melolontha*, and *Popillia japonica*;
- (m) insect pests of the family Scolytidae, for example, *Ips typographus*;
- (n) insect pests of the family Staphylinidae, for example, *Paederus fuscipes*;
- (o) insect pests of the family Tenebrionidae, for example, *Tenebrio molitor* and *Tribolium castaneum*;

(p) insect pests of the family Trogossitidae, for example, *Tenebroides mauritanicus*.

(5) Insect Pests of the Order Diptera (A) the Suborder Brachycera
- (a) insect pests of the family Agromyzidae, for example, *Liriomyza bryoniae*, *Liriomyza chinensis*, *Liriomyza sativae*, and *Liriomyza trifolii* of *Liriomyza* spp.; and *Chromatomyia horticola* and *Agromyza oryzae*;
- (b) insect pests of the family Anthomyiidae, for example, *Delia platura* and *Delia radicum* of *Delia* spp.; and *Pegomya cunicularia*;
- (c) insect pests of the family Drosophilidae, for example, *Drosophila melanogaster* and *Drosophila suzukii* of *Drosophila* spp.;
- (d) insect pests of the family Ephydridae, for example, *Hydrellia griseola*;
- (e) insect pests of the family Psilidae, for example, *Psila rosae*;
- (f) insect pests of the family Tephritidae, for example, *Bactrocera cucurbitae* and *Bactrocera dorsalis* of *Bactrocera* spp.; for example, *Rhagoletis cerasi* and *Rhagoletis pomonella* of *Rhagoletis* spp.; and *Ceratitis capitata* and *Dacus oleae*.

(B) The Suborder Nematocera
- (a) insect pests of the family Cecidomyiidae, for example, *Asphondylia yushimai*, *Contarinia sorghicola*, *Mayetiola destructor*, and *Sitodiplosis mosellana*.

(6) Insect Pests of the Order Orthoptera
- (a) insect pests of the family Acrididae, for example, *Schistocerca americana* and *Schistocerca gregaria* of *Schistocerca* spp.; and *Chortoicetes terminifera*, *Dociostaurus maroccanus*, *Locusta migratoria*, *Locustana pardalina*, *Nomadacris septemfasciata*, and *Oxya yezoensis*;
- (b) insect pests of the family Gryllidae, for example, *Acheta domestica* and *Teleogryllus emma*;
- (c) insect pests of the family Gryllotalpidae, for example, *Gryllotalpa orientalis*;
- (d) insect pests of the family Tettigoniidae, for example, *Tachycines asynamorus*.

(7) Acari (A) Acaridida of the Order Astigmata
- (a) acari of the family Acaridae, for example, *Rhizoglyphus echinopus* and *Rhizoglyphus robini* of *Rhizoglyphus* spp.; for example, *Tyrophagus neiswanderi*, *Tyrophagus perniciosus*, *Tyrophagus putrescentiae*, and *Tyrophagus similis* of *Tyrophagus* spp.; and *Acarus siro*, *Aleuroglyphus ovatus*, and *Mycetoglyphus fungivorus*;

(B) Actinedida of the Order Prostigmata
- (a) acari of the family Tetranychidae, for example, *Bryobia praetiosa* and *Bryobia rubrioculus* of *Bryobia* spp.; for example, *Eotetranychus asiaticus*, *Eotetranychus boreus*, *Eotetranychus celtis*, *Eotetranychus geniculatus*, *Eotetranychus kankitus*, *Eotetranychus pruni*, *Eotetranychus shii*, *Eotetranychus smithi*, *Eotetranychus suginamensis*, and *Eotetranychus uncatus* of *Eotetranychus* spp.; for example, *Oligonychus hondoensis*, *Oligonychus ilicis*, *Oligonychus karamatus*, *Oligonychus mangiferus*, *Oligonychus orthius*, *Oligonychus perseae*, *Oligonychus pustulosus*, *Oligonychus shinkajii*, and *Oligonychus ununguis* of *Oligonychus* spp.; for example, *Panonychus citri*, *Panonychus mori*, and *Panonychus ulmi* of *Panonychus* spp.; for example, *Tetranychus cinnabarinus*, *Tetranychus kanzawai*, *Tetranychus ludeni*, *Tetranychus quercivorus*, *Tetranychus phaselus*, *Tetranychus urticae*, *Tetranychus viennensis*, and *Tetranychus evansi* of *Tetranychus* spp.; for example, *Aponychus corpuzae* and *Aponychus firmianae* of *Aponychus* spp.; for example, *Sasanychus akitanus* and *Sasanychus pusillus* of *Sasanychus* spp.; for example, *Schizotetranychus celarius*, *Schizotetranychus longus*, *Schizotetranychus miscanthi*, *Schizotetranychus recki*, and *Schizotetranychus schizopus* of *Schizotetranychus* spp.; and *Tetranychina harti*, *Tuckerella pavoniformis*, and *Yezonychus sapporensis*;
- (b) acari of the family Tenuipalpidae, for example, *Brevipalpus lewisi*, *Brevipalpus obovatus*, *Brevipalpus phoenicis*, *Brevipalpus russulus*, and *Brevipalpus californicus* of *Brevipalpus* spp.; for example, *Tenuipalpus pacificus* and *Tenuipalpus zhizhilashviliae* of *Tenuipalpus* spp.; and *Dolichotetranychus floridanus*;
- (c) acari of the family Eriophyidae, for example, *Aceria diospyri*, *Aceria ficus*, *Aceria japonica*, *Aceria kuko*, *Aceria paradianthi*, *Aceria tiyingi*, *Aceria tulipae*, and *Aceria zoysiea* of *Aceria* spp.; for example, *Eriophyes chibaensis* and *Eriophyes emarginatae* of *Eriophyes* spp.; for example, *Aculops lycopersici* and *Aculops pelekassi* of *Aculops* spp.; for example, *Aculus fockeui* and *Aculus schlechtendali* of *Aculus* spp.; and *Acaphylla theavagrans*, *Calacarus carinatus*, *Colomerus vitis*, *Calepitrimerus vitis*, *Epitrimerus pyri*, *Paraphytoptus kikus*, *Paracalacarus podocarpi*, and *Phyllocotruta citri*;
- (d) acari of the family Tarsonemidae, for example, *Tarsonemus bilobatus* and *Tarsonemus waitei* of *Tarsonemus* spp.; and *Phytonemus pallidus* and *Polyphagotarsonemus latus*;
- (e) acari of the family Penthaleidae, for example, *Penthaleus erythrocephalus* and *Penthaleus major* of *Penthaleus* spp.

[Ectoparasite Control Agent]

The ectoparasite control agent of the present invention contains at least one active ingredient selected from the (hetero)aryl imidazole compounds of the present invention. The amount of the (hetero)aryl imidazole compound contained in the ectoparasite control agent of the present invention is not particularly limited as long as its ectoparasite control effect is exhibited.

As the host animal to be treated with the ectoparasite control agent of the present invention, a warm-blooded animal such as a human and a livestock mammal (e.g., a cow, a horse, a pig, sheep, and a goat), a laboratory animal (e.g., a mouse, a rat, and a sand rat), a pet animal (e.g., a hamster, a guinea pig, a dog, a cat, a horse, a squirrel, a rabbit, and a ferret), wild and zoo mammals (e.g., a monkey, a fox, a deer, and a buffalo), a fowl (e.g., a turkey, a duck, a chicken, a quail, and a goose), and a pet bird (e.g., a pigeon, a parrot, a myna bird, a Java sparrow, a parakeet, a Bengalese finch, and a canary bird); and fishes such as salmon, trout, and carp may be exemplified. In addition, a bee, a stag beetle and a beetle may be exemplified.

The ectoparasite control agent of the present invention may be applied by a known veterinary approach (local, oral, parenteral or subcutaneous administration). As the method therefor, a method of orally administering tablets, capsules, feed or the like containing the ectoparasite control agent to animals; a method of administering the ectoparasite control agent through dipping liquids, suppositories, injection (intramuscular, subcutaneous, intravenous, or intraperitoneal injection, etc.) or the like to animals; a method of locally administering oily or aqueous liquid formulations by spraying, pour-on, spot-on or the like; and a method of kneading the ectoparasite control agent into a resin, shaping the kneaded product into a suitable shape such as a collar or an ear tag, and attaching it to animals for local administration; or the like may be exemplified.

Ectoparasites parasitize the inside or the body surface of host animals, particularly, warm-blooded animals. Specifically, the ectoparasites parasitize the backs, armpits, lower abdomens, inner thighs, or the like of host animals and live by obtaining nutrients such as blood or dandruff from the animals. As the ectoparasite, acari, lice, fleas, a mosquito, a stable fly, a flesh fly or the like may be exemplified. Specific examples of the ectoparasite controllable with the ectoparasite control agent of the present invention will be shown below.

(1) Acari acari of the family Dermanyssidae, acari of the family Macronyssidae, acari of the family Laelapidae, acari of the family Varroidae, acari of the family Argasidae, acari of the family Ixodidae, acari of the family Psoroptidae, acari of the family Sarcoptidae, acari of the family Knemidokoptidae, acari of the family Demodixidae, acari of the family Trombiculidae, and insect parasitic acari such as acari of the family Canestriniidae.

(2) The order Phthiraptera lice of the family Haematopinidae, lice of the family Linognathidae, bird lice of the family Menoponidae, bird lice of the family Philopteridae, and bird lice of the family Trichodectidae.

(3) The order Siphonaptera fleas of the family Pulicidae, for example, *Ctenocephalides canis* and *Ctenocephalides felis* of *Ctenocephalides* spp.;

fleas of the family Tungidae, fleas of the family Ceratophyllidae, and fleas of the family Leptopsyllidae.

(4) The order Hemiptera (5) Insect pests of the order Diptera mosquitos of the family Culicidae, black flies of the family Simuliidae, biting midges of the family Ceratopogonidae, horseflies of the family Tabanidae, flies of the family Muscidae, tsetse flies of the family Glossinidae, flesh flies of the family Sarcophagidae, flies of the family Hippoboscidae, flies of the family Calliphoridae, and flies of the family Oestridae.

[Endoparasite Control Agent or Expellant]

The endoparasite control agent or expellant of the present invention contains at least one active ingredient selected from the (hetero)aryl imidazole compounds of the present invention. The amount of the (hetero)aryl imidazole compound contained in the endoparasite control agent or expellant of the present invention is not particularly limited as long as its endoparasite control effect is exhibited.

The parasite targeted by the endoparasite control agent or expellant of the present invention parasitizes the inside of host animals, particularly, warm-blooded animals or fishes (endoparasite). As the host animal for which the endoparasite control agent or expellant of the present invention is effective, a warm-blooded animal such as a human and a livestock mammal (e.g., a cow, a horse, a pig, sheep, and a goat), a laboratory animal (e.g., a mouse, a rat, and a sand rat), a pet animal (e.g., a hamster, a guinea pig, a dog, a cat, a horse, a squirrel, a rabbit, and a ferret), wild and zoo mammals (e.g., a monkey, a fox, a deer, and a buffalo), a fowl (e.g., a turkey, a duck, a chicken, a quail, and a goose), and a pet bird (e.g., a pigeon, a parrot, a myna bird, a Java sparrow, a parakeet, a Bengalese finch, and a canary bird); and fishes such as salmon, trout, and carp may be exemplified. Parasitic diseases mediated by parasites may be prevented or treated by controlling and expelling the parasites.

As the parasite to be controlled or expelled, the following may be exemplified.

(1) Nematodes of the Order Dioctophymatida
   (a) kidney worms of the family Dioctophymatidae, for example, *Dioctophyma renale* of *Dioctophyma* spp.;
   (b) kidney worms of the family Soboliphymatidae, for example, *Soboliphyme abei* and *Soboliphyme baturini* of *Soboliphyme* spp.

(2) Nematodes of the Order Trichocephalida
   (a) trichinae of the family Trichinellidae, for example, *Trichinella spiralis* of *Trichinella* spp.;
   (b) whipworms of the family Trichuridae, for example, *Capillaria annulata, Capillaria contorta, Capillaria hepatica, Capillaria perforans, Capillaria plica*, and *Capillaria suis* of *Capillaria* spp.; and *Trichuris vulpis, Trichuris discolor, Trichuris ovis, Trichuris skrjabini*, and *Trichuris suis* of *Trichuris* spp.

(3) Nematodes of the Order Rhabditida
   threadworms of the family Strongyloididae, for example, *Strongyloides papillosus, Strongyloides planiceps, Strongyloides ransomi, Strongyloides suis, Strongyloides stercoralis, Strongyloides tumefaciens*, and *Strongyloides ratti* of *Strongyloides* spp.

(4) Nematodes of the Order Strongylida
   hookworms of the family Ancylostomatidae, for example, *Ancylostoma braziliense, Ancylostoma caninum, Ancylostoma duodenale*, and *Ancylostoma tubaeforme* of *Ancylostoma* spp.; *Uncinaria stenocephala* of *Uncinaria* spp.; and *Bunostomum phlebotomum* and *Bunostomum trigonocephalum* of *Bunostomum* spp.

(5) Nematodes of the Order Strongylida
   (a) nematodes of the family Angiostrongylidae, for example, *Aelurostrongylus abstrusus* of *Aelurostrongylus* spp.; and *Angiostrongylus vasorum* and *Angiostrongylus cantonesis* of *Angiostrongylus* spp.;
   (b) nematodes of the family Crenosomatidae, for example, *Crenosoma aerophila* and *Crenosoma vulpis* of *Crenosoma* spp.;
   (c) nematodes of the family Filaroididae, for example, *Filaroides hirthi* and *Filaroides osleri* of *Filaroides* spp.;
   (d) lungworms of the family Metastrongylidae, for example, *Metastrongylus apri, Metastrongylus asymmetricus, Metastrongylus pudendotectus*, and *Metastrongylus salmi* of *Metastrongylus* spp.;
   (e) gapeworms of the family Syngamidae, for example, *Cyathostoma bronchialis* of *Cyathostoma* spp.; and *Syngamus skrjabinomorpha* and *Syngamus trachea* of *Syngamus* spp.

(6) Nematodes of the Order Strongylida
   (a) nematodes of the family Molineidae, for example, *Nematodirus filicollis* and *Nematodirus spathiger* of *Nematodirus* spp.;
   (b) nematodes of the family Dictyocaulidae, for example, *Dictyocaulus filaria* and *Dictyocaulus viviparus* of *Dictyocaulus* spp.;
   (c) nematodes of the family Haemonchidae, for example, *Haemonchus contortus* of *Haemonchus* spp.; and *Mecistocirrus digitatus* of *Mecistocirrus* spp.;
   (d) nematodes of the family Haemonchidae, for example, *Ostertagia ostertagi* of *Ostertagia* spp.;
   (e) nematodes of the family Heligmonellidae, for example, *Nippostrongylus braziliensis* of *Nippostrongylus* spp.;

(f) nematodes of the family Trichostrongylidae, for example, *Trichostrongylus axei*, *Trichostrongylus colubriformis*, and *Trichostrongylus tennis* of *Trichostrongylus* spp.; *Hyostrongylus rubidus* of *Hyostrongylus* spp.; and *Obeliscoides cuniculi* of *Obeliscoides* spp.

(7) Nematodes of the Order Strongylida
  (a) nematodes of the family Chabertiidae, for example, *Chabertia ovina* of *Chabertia* spp.; and *Oesophagostomum brevicaudatum*, *Oesophagostomum columbianum*, *Oesophagostomum dentatum*, *Oesophagostomum georgianum*, *Oesophagostomum maplestonei*, *Oesophagostomum quadrispinulatum*, *Oesophagostomum radiatum*, *Oesophagostomum venulosum*, and *Oesophagostomum watanabei* of *Oesophagostomum* spp.;
  (b) nematodes of the family Stephanuridae, for example, *Stephanurus dentatus* of *Stephanurus* spp.;
  (c) nematodes of the family Strongylidae, for example, *Strongylus asini*, *Strongylus edentatus*, *Strongylus equinus*, and *Strongylus vulgaris* of *Strongylus* spp.

(8) Nematodes of the Order Oxyurida
  nematodes of the family Oxyuridae, for example, *Enterobius anthropopitheci* and *Enterobius vermicularis* of *Enterobius* spp.; *Oxyuris equi* of *Oxyuris* spp.; and *Passalurus ambiguous* of *Passalurus* spp.

(9) Nematodes of the Order Ascaridida
  (a) nematodes of the family Ascaridiidae, for example, *Ascaridia galli* of *Ascaridia* spp.;
  (b) nematodes of the family Heterakidae, for example, *Heterakis beramporia*, *Heterakis brevispiculum*, *Heterakis gallinarum*, *Heterakis pusilla*, and *Heterakis putaustralis* of *Heterakis* spp.;
  (c) nematodes of the family Anisakidae, for example, *Anisakis simplex* of *Anisakis* spp.;
  (d) nematodes of the family Ascarididae, for example, *Ascaris lumbricoides* and *Ascaris suum* of *Ascaris* spp.; and *Parascaris equorum* of *Parascaris* spp.;
  (e) nematodes of the family Toxocaridae, for example, *Toxocara canis*, *Toxocara leonina*, *Toxocara suum*, *Toxocara vitulorum*, and *Toxocara cati* of *Toxocara* spp.

(10) Nematodes of the Order Spirurida
  (a) nematodes of the family Onchocercidae, for example, *Brugia malayi*, *Brugia pahangi*, and *Brugia patei* of *Brugia* spp.; *Dipetalonema reconditum* of *Dipetalonema* spp.; *Dirofilaria immitis* of *Dirofilaria* spp.; *Filaria oculi* of *Filaria* spp.; and *Onchocerca cervicalis*, *Onchocerca gibsoni*, and *Onchocerca gutturosa* of *Onchocerca* spp.;
  (b) nematodes of the family Setariidae, for example, *Setaria digitata*, *Setaria equina*, *Setaria labiatopapillosa*, and *Setaria marshalli* of *Setaria* spp.; and *Wuchereria bancrofti* of *Wuchereria* spp.;
  (c) nematodes of the family Filariidae, for example, *Parafilaria multipapillosa* of *Parafilaria* spp.; and *Stephanofilaria assamensis*, *Stephanofilaria dedoesi*, *Stephanofilaria kaeli*, *Stephanofilaria okinawaensis*, and *Stephanofilaria stilesi* of *Stephanofilaria* spp.

(11) Nematodes of the Order Spirurida
  (a) nematodes of the family Gnathostomatidae, for example, *Gnathostoma doloresi* and *Gnathostoma spinigerum* of *Gnathostoma* spp.;
  (b) nematodes of the family Habronematidae, for example, *Habronema majus*, *Habronema microstoma*, and *Habronema muscae* of *Habronema* spp.; and *Draschia megastoma* of *Draschia* spp.;
  (c) nematodes of the family Physalopteridae, for example, *Physaloptera canis*, *Physaloptera cesticillata*, *Physaloptera erdocyona*, *Physaloptera felidis*, *Physaloptera gemina*, *Physaloptera papilloradiata*, *Physaloptera praeputialis*, *Physaloptera pseudopraerutialis*, *Physaloptera rara*, *Physaloptera sibirica*, and *Physaloptera vulpineus* of *Physaloptera* spp.;
  (d) nematodes of the family Gongylonematidae, for example, *Gongylonema pulchrum* of *Gongylonema* spp.;
  (e) nematodes of the family Spirocercidae, for example, *Ascarops strongylina* of *Ascarops* spp.;
  (f) nematodes of the family Thelaziidae, for example, *Thelazia callipaeda*, *Thelazia gulosa*, *Thelazia lacrymalis*, *Thelazia rhodesi*, and *Thelazia skrjabini* of *Thelazia* spp.

[Control Agent for Other Pests]

The (hetero)aryl imidazole compound of the present invention is additionally excellent in control effect on insect pests that have a stinger or venom and harm humans and animals, insect pests that mediate various pathogens or disease-causing microbes, or insect pests that cause discomfort to humans (toxic pests, hygienic pests, and obnoxious pests, etc.).

Specific examples thereof will be shown below.

(1) Insect Pests of the Order Hymenoptera
  bees of the family Argidae, bees of the family Cynipidae, bees of the family Diprionidae, ants of the family Formicidae, bees of the family Mutillidae, and bees of the family Vespidae.

(2) Other Insect Pests
  Blattodea, termites, Araneae, centipedes, millipedes, crustacea, and *Cimex lectularius*.

[Seed Treatment Agent or Vegetative Propagation Organ Treatment Agent]

The seed treatment agent or vegetative propagation organ treatment agent of the present invention contains at least one active ingredient selected from the (hetero)aryl imidazole compounds of the present invention. The amount of the (hetero)aryl imidazole compound contained in the seed treatment agent or vegetative propagation organ treatment agent of the present invention is not particularly limited as long as its control effect is exhibited.

The vegetative propagation organ means a plant root, stem, leaf, or the like having the ability to grow when the site is separated from the body and placed in soil. As the vegetative propagation organ, for example, a tuberous root, a creeping root, a bulb, a corm or solid bulb, a tuber, a rhizome, a stolon, a rhizophore, cane cuttings, a propagule and a vine cutting are exemplified. The stolon is also called runner. The propagule is also called bulblet and is classified into a broad bud and a bulbil. The vine cutting means a shoot (generic name for leaves and stems) of sweet potato, Japanese yam, or the like. The bulb, the corm or solid bulb, the tuber, the rhizome, the cane cutting, the rhizophore and the tuberous root are also collectively called flower bulb. The cultivation of tubers and roots is started by planting tubers in soil. The tubers used are generally called seed tubers.

The seed treatment agent or vegetative propagation organ treatment agent of the present invention refers to a preparation such as a wettable powder, wettable granules, a flowable concentrate, or a dust formulated by mixing at least one active ingredient selected from the (hetero)aryl imidazole compounds of the present invention with an appropriate solid carrier or liquid carrier, and, if necessary, adding a surfactant or other formulation adjuvants to the mixture. Also, the composition may contain a binder. As the composition containing a binder, a flowable concentrate (FS) for seed treatment is exemplified.

An adhesive substance that does not phytotoxically affect plant seeds or vegetative propagation organs is used as the binder. Specifically, at least one substance selected from the group consisting of polyvinyl acetate, polyvinyl alcohol, cellulose including ethylcellulose, methylcellulose, hydroxymethylcellulose, hydroxypropylcellulose, and carboxymethylcellulose, polyvinylpyrrolidone, starch, modified starch, dextrin, maltodextrin, polysaccharides including alginate and chitosan, proteins including gelatin and casein, gum arabic, shellac, calcium lignosulfonate, and a methacrylamide monomer may be used.

Pests may be efficiently controlled by treating seed tubers with at least one compound selected from the (hetero)aryl imidazole compounds of the present invention. As the method for treating a seed tuber with the (hetero)aryl imidazole compound, dipping treatment, dust coating treatment, coating treatment or the like is exemplified. For the planting of seed tubers using a tractor, the seed tubers may be treated by spraying a chemical containing the (hetero)aryl imidazole compound onto the seed tubers on the tractor.

[Granular Agrochemical Composition for Paddy Rice Seedling Nursery Box Treatment]

The granular agrochemical composition for paddy rice seedling nursery box treatment (hereinafter, referred to as the "granular agrochemical composition") of the present invention contains at least one active ingredient selected from the (hetero)aryl imidazole compounds of the present invention. The amount of the (hetero)aryl imidazole compound contained in the granular agrochemical composition of the present invention is not particularly limited as long as its control effect is exhibited.

The granular agrochemical composition may be obtained by various methods, but is obtained, for example, by the extrusion granulation or the like of a powdery composition combined one or more active ingredients with a surfactant, a binder and an inorganic carrier, etc., if necessary, by using a wet granulation method. More specifically, the active ingredient adjusted to a predetermined particle size was uniformly mixed with a necessary surfactant, binder and inorganic carrier. Then, an appropriate amount of water is added thereto, and the mixture is kneaded, shaped by extrusion through a screen having opened pores, and dried to prepare a granular agrochemical composition. The size of the pores used in this operation is usually preferably 0.5 mm to 1.5 mm.

The particle size of the granular agrochemical composition thus obtained is not particularly limited, but is preferably 0.5 mm to 1.5 mm, and particularly preferably 0.7 mm to 1.5 mm, in terms of average particle size. The granules having such a particle size are obtained by granulation, drying and subsequent sifting.

In the granular agrochemical composition, if necessary, a surfactant, a binder and an inorganic carrier are combined. Among them, as the surfactant, for example, a nonionic surfactant such as polyethylene glycol higher fatty acid ester, polyoxyethylene alkyl ether, polyoxyethylene alkyl aryl ether, polyoxyethylene aryl phenyl ether, and sorbitan monoalkylate; an anionic surfactant such as alkyl aryl sulfonate, dialkyl sulfonate, alkyl sulfuric acid ester salt, alkyl phosphoric acid ester salt, alkyl aryl sulfuric acid ester salt, alkyl aryl phosphoric acid ester salt, polyoxyethylene alkyl ether sulfuric acid ester salt, naphthalenesulfonic acid salt and a condensate thereof, ligninsulfonic acid salt, polycarboxylic acid-type polymer surfactant such as a copolymer of acrylic acid and itaconic acid or a copolymer of meth- acrylic acid and itaconic acid, a copolymer of maleic acid and styrene, a copolymer of maleic acid and diisobutylene and their alkali metal salts; polyoxyethylene aryl phenyl ether phosphoric acid ester salt; polyoxyethylene aryl phenyl ether sulfuric acid ester salt, or the like is exemplified. The amount of this surfactant added is usually 0.1 parts by weight to 5 parts by weight, though the amount is not particularly limited.

As the binder to be combined in the granular agrochemical composition, for example, carboxymethylcellulose metal salt, polyvinyl alcohol, pregelatinized starch, dextrin, xanthan gum, guar seed gum, sucrose, polyvinylpyrrolidone, polyacrylic acid metal salt or the like is exemplified. The amount of the binder combined is usually 0.1 parts by weight to 5 parts by weight, though the amount is not particularly limited. The inorganic carrier to be combined in the granules is not particularly limited. For example, clays, calcium carbonate, talc, diatomaceous earth, zeolite, attapulgite, gypsum, porcelain stone or the like is exemplified.

[Soil Treatment Agent]

The soil treatment according to the present invention is, for example, a method of directly controlling pests by applying an active ingredient to the rhizospheres of plants to be protected from harm such as eating by the pest, or controlling pests by penetrating and transporting an active ingredient to the inside of plant bodies from their roots or the like. Specifically, for example, planting hole treatment (planting hole spraying and planting hole soil-incorporation), plant foot treatment (plant foot spraying, plant foot soil-incorporation, plant foot irrigation, and plant foot treatment at latter half of the seedling raising period), planting furrow treatment (planting furrow spraying and planting furrow soil-incorporation), planting row treatment (planting row spraying, planting row soil-incorporation, and planting row spraying at the growing period), planting row treatment at sowing (planting row spraying at sowing and planting row soil-incorporation at sowing), broadcast treatment (broadcast soil spraying and broadcast soil-incorporation), band dressing, submerged treatment (broadcast submerged application and frame submerged application), other soil spraying treatments (foliar granule spraying at the growing period, spraying under tree crowns or around main stems, soil surface spraying, soil surface incorporation, sowing hole spraying, surface spraying on the ribbing ground, and interplant spraying), other irrigation treatments (soil irrigation, irrigation at the seedling raising period, chemical injection treatment, irrigation on the plant foot, chemical drip irrigation, and chemigation), seedling nursery box treatment (seedling nursery box spraying, seedling nursery box irrigation, and seedling nursery box chemical flooding), seedling nursery tray treatment (seedling nursery tray spraying, seedling nursery tray irrigation, and flooded nursery tray spraying), nursery bed treatment (nursery bed spraying, nursery bed irrigation, flooded nursery bed spraying), seedling dipping, nursery soil-incorporation treatment (seedbed soil-incorporation and cover soil-incorporation), spraying before soil covering at sowing, spraying after soil covering at sowing, stem injection treatment, trunk injection treatment, trunk spraying treatment, and other treatments (plowing, surface soil-incorporation, soil incorporation into rain dropping lines, planting spot treatment, flower cluster granule spraying, and paste fertilizer mixing) are exemplified.

[Bait Agent]

The bait agent of the present invention contains at least one active ingredient selected from the (hetero)aryl imidazole compounds of the present invention. The amount of the (hetero)aryl imidazole compound contained in the bait agent of the present invention is not particularly limited as long as its control effect is exhibited.

The bait agent of the present invention may contain, if necessary, an ingestibility improving component such as a sugar, a carbohydrate, or a milk constituent, a synergist, an aversive agent to prevent accidental ingestion, a preservative, a flavor, an attractant, or the like. The bait agent of the present invention may usually be prepared by mixing the (hetero)aryl imidazole compound with water and, if necessary, other components described above. In the preparation of the bait agent of the present invention, the (hetero)aryl imidazole compound may be the (hetero)aryl imidazole compound itself, or may be in the form of a formulation such as a dust, a wettable powder, a microcapsule, or a flowable concentrate.

As the pest that may be effectively controlled with the bait agent of the present invention, a cockroach such as *Periplaneta americana, Blattella germanica*, and *Periplaneta fuliginosa*, a click beetle such as *Melanotus okinawensis*, an ant such as *Monomorium intrudens* and *Formica fusca*, a deathwatch beetle such as *Lasioderma serricorne* and *Stegobium paniceum*, a flour beetle such as *Tribolium castaneum* and *Tribolium confusum*, a flat bark beetle such as *Oryzaephilus surinamensis* and *Cryptolestes pusillus*, a white ant such as *Coptotermes formosanus* and *Reticulitermes speratus*, a fly such as *Musca domestica, Fannia canicularis, Phoridae*, and *Phlebotominae*, and a mosquito such as *Culex pipiens, Aedes albopictus*, anopheles, and chironomids are exemplified.

The bait agent of the present invention may be applied as it is, or by impregnating a nonwoven fabric, sponge, absorbent cotton, or the like, for example. This aqueous bait agent or the nonwoven fabric, sponge, absorbent cotton, or the like impregnated with the bait agent is placed in a container such as a cup, a tray, or a bottle, for example, and subjected to insect pest expelling. In this respect, the apparatus for expelling insect pest which is equipped with the container covered outside and have some degree of space where insect pests are capable of residing in order to ingest the bait agent of the present invention generally improves ingestibility and is thus effective.

[Plant Growth Promoter]

The plant growth promoter of the present invention contains at least one active ingredient selected from the (hetero) aryl imidazole compounds of the present invention. The amount of the (hetero)aryl imidazole compound contained in the plant growth promoter of the present invention is not particularly limited as long as its effect of promoting plant growth is exhibited.

In the plant growth promoter of the present invention, if necessary, other components, a carrier, or the like may be appropriately combined.

The (hetero)aryl imidazole compound of the present invention may be used alone as a plant growth promoter, but may usually be used as a formulation in a dosage form such as a wettable powder, a liquid formulation, an oil formulation, a dust, a granular formulation, or a suspension concentrate (flowable) by mixing the (hetero)aryl imidazole compound as an active ingredient with common adjuvants for formulation use, such as a solid carrier, a liquid carrier, a dispersant, a diluent, an emulsifier, a spreading agent and a thickener.

As the solid carrier or the liquid carrier, for example, talc, clay, bentonite, kaolin, diatomaceous earth, montmorillonite, mica, vermiculite, gypsum, calcium carbonate, white carbon, wood flour, starch, alumina, silicate, glycopolymer, waxes, water, alcohols (methyl alcohol, ethyl alcohol, n-propyl alcohol, isopropyl alcohol, n-butyl alcohol, ethylene glycol, benzyl alcohol, etc.), a petroleum fraction (petroleum ether, kerosene, solvent naphtha, etc.), aliphatic or alicyclic hydrocarbons (n-hexane, cyclohexane, etc.), aromatic hydrocarbons (benzene, toluene, xylene, ethylbenzene, chlorobenzene, cumene, methylnaphthalene, etc.), halogenated hydrocarbons (chloroform, dichloromethane, etc.), ethers (isopropyl ether, ethylene oxide, tetrahydrofuran, etc.), ketones (acetone, methyl ethyl ketone, cyclohexanone, methyl isobutyl ketone, etc.), esters (ethyl acetate, butyl acetate, ethylene glycol acetate, amyl acetate, etc.), acid amides (dimethylformamide, dimethylacetanilide, etc.), nitriles (acetonitrile, propionitrile, acrylonitrile, etc.), sulfoxides (dimethyl sulfoxide, etc.), alcohol ethers (ethylene glycol monomethyl ether, ethylene glycol monoethyl ether, etc.) or the like is exemplified.

As the adjuvant, for example, a nonionic surfactant (polyoxyethylene alkyl ether, polyoxyethylene alkyl ester, polyoxyethylene alkyl phenyl ether, polyoxyethylene sorbitan alkyl ester, sorbitan alkyl ester, etc.), an anionic surfactant (alkyl benzenesulfonate, alkyl sulfosuccinate, polyoxyethylene alkyl sulfate, aryl sulfonate, etc.), a cationic surfactant (alkylamines, polyoxyethylene alkylamines, quaternary ammonium salts, etc.), an amphoteric surfactant (alkylaminoethylglycine, alkyldimethylbetaine, etc.), polyvinyl alcohol, hydroxypropylcellulose, carboxymethylcellulose, gum arabic, tragacanth gum, xanthan gum, polyvinyl acetate, gelatin, casein, sodium alginate or the like is exemplified.

As other components, other active ingredients such as the fungicide, insecticide or acaricide, nematicide, and pesticide for soil insect pests described above; a plant regulating agent, a synergist, a fertilizer, a soil improvement agent, animal feed or the like is exemplified.

The content of the (hetero)aryl imidazole compound of the present invention in the plant growth promoter differs variously depending on a preparation form, an application method, and other conditions, but is preferably 0.5 to 95% by weight, and particularly preferably in the range of 2 to 70% by weight.

The plant to which the plant growth promoter is to be applied is not particularly limited. For example, cereals of the family Poaceae, such as rice, barley, wheat, Japanese millet, corn, and foxtail millet; vegetables such as pumpkin, turnip, cabbage, daikon radish, Chinese cabbage, spinach, bell pepper, and tomato; flowers and ornamental plants such as chrysanthemum, gerbera, pansy, orchid, peony, and tulip; beans such as azuki bean, kidney bean, soybean, peanut, broad bean, and garden pea; tubers and roots such as potato, sweet potato, eddo, Japanese yam, and taro; *Allium* such as green onion, onion, and rakkyo, or the like is exemplified.

As for a method for applying the plant growth promoter of the present invention, application to plants (foliage application), application to plant growing soil (soil application), application to paddy water (submerged application), application to seeds (seed treatment), or the like is possible.

The applied amount of the plant growth promoter of the present invention differs depending on a plant to which the plant growth promoter is applied, etc., but is in the range of 1 to 10000 ppm in terms of active ingredient concentration and preferably 50 to 300 L/10 are of a solution containing 10 to 1000 ppm of the active ingredient, for foliage application, is preferably 0.1 to 1000 g/10 are and particularly preferably 10 to 100 g/10 are, of the active ingredient for soil application and submerged application. Also, 0.001 to 50 g of the active ingredient is preferably applied per kg of seeds for seed treatment.

[Formulation Preparation]

Some formulation preparations of the pest control agent, the insecticide or acaricide, the ectoparasite control agent or the endoparasite control agent or expellant of the present invention will be shown. However, additives and addition ratios should not be limited by these examples and may be changed in wide ranges. The term "part" in the formulation preparations represents part by weight.

Hereinafter, the formulation preparations for agriculture or horticulture and for paddy rice will be shown.

(Formulation 1: Wettable Powder)

40 parts of the (hetero)aryl imidazole compound of the present invention, 53 parts of diatomaceous earth, 4 parts of higher alcohol sulfuric acid ester, and 3 parts of alkyl naphthalenesulfonate are uniformly mixed and finely milled to obtain a wettable powder containing 40% of the active ingredient.

(Formulation 2: Emulsion)

30 parts of the (hetero)aryl imidazole compound of the present invention, 33 parts of xylene, 30 parts of dimethylformamide, and 7 parts of polyoxyethylene alkyl allyl ether are mixed and dissolved to obtain an emulsion containing 30% of the active ingredient.

(Formulation 3: Granular Formulation)

5 parts of the (hetero)aryl imidazole compound of the present invention, 40 parts of talc, 38 parts of clay, 10 parts of bentonite, and 7 parts of sodium alkyl sulfate are uniformly mixed, finely milled, and then granulated into a granular shape of 0.5 to 1.0 mm in diameter to obtain a granular formulation containing 5% of the active ingredient.

(Formulation 4: Granular Formulation)

5 parts of the (hetero)aryl imidazole compound of the present invention, 73 parts of clay, 20 parts of bentonite, 1 part of dioctyl sulfosuccinate sodium salt, and 1 part of potassium phosphate are well milled and mixed, and after addition of water, the mixture is well kneaded, then granulated, and dried to obtain a granular formulation containing 5% of the active ingredient.

(Formulation 5: Suspension)

10 parts of the (hetero)aryl imidazole compound of the present invention, 4 parts of polyoxyethylene alkyl allyl ether, 2 parts of polycarboxylic acid sodium salt, 10 parts of glycerin, 0.2 parts of xanthan gum, and 73.8 parts of water are mixed and wet-milled until the particle size becomes 3 microns or smaller to obtain a suspension containing 10% of the active ingredient.

Hereinafter, the formulation preparations of the ectoparasite control agent or the endoparasite control agent or expellant will be shown.

(Formulation 6: Granules)

5 parts of the (hetero)aryl imidazole compound of the present invention are dissolved in an organic solvent to obtain a solution. The solution is sprayed onto 94 parts of kaolin and 1 part of white carbon. Then, the solvent is evaporated under reduced pressure. This type of granules may be mixed with animal feed.

(Formulation 7: Injectable Filler)

0.1 to 1 parts of the (hetero)aryl imidazole compound of the present invention and 99 to 99.9 parts of peanut oil are uniformly mixed and then sterilized by filtration through a sterilizing filter.

(Formulation 8: Pore-On Formulation)

5 parts of the (hetero)aryl imidazole compound of the present invention, 10 parts of myristic acid ester, and 85 parts of isopropanol are uniformly mixed to obtain a pore-on formulation.

(Formulation 9: Spot-On Formulation)

1 to 15 parts of the (hetero)aryl imidazole compound of the present invention, 10 parts of palmitic acid ester, and 75 to 80 parts of isopropanol are uniformly mixed to obtain a spot-on formulation.

(Formulation 10: Spray Formulation)

1 part of the (hetero)aryl imidazole compound of the present invention, 10 parts of propylene glycol, and 89 parts of isopropanol are uniformly mixed to obtain a spray formulation.

Next, the present invention will be more specifically described with reference to Examples of compounds. However, the present invention is not limited by the following Examples of compounds by any means.

Example 1

Synthesis of 2-(5-(2-chloro-3,3,3-trifluoroprop-1-en-1-yl)-1-methyl-1H-imidazol-2-yl)-5-cyclopropyl-3-(ethylsulfonyl)pyridine (Compound No. d-2)

(Step 1) Synthesis of 5-bromo-3-(ethylthio)picolinonitrile

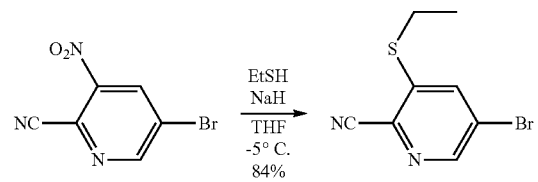

In a reaction vessel, 5-bromo-3-nitropicolinonitrile (1 g) was dissolved in tetrahydrofuran (22 ml), and the reaction vessel was replaced with nitrogen. Then, the solution was cooled to −5° C. and stirred. Ca. 60% sodium hydride (0.2 g) was added thereto, and the mixture was stirred at −5° C. for 5 minutes. Then, ethylmercaptan (0.27 g) was added dropwise thereto, and the mixture was stirred at −5° C. for 30 minutes. The obtained solution was poured into water, and extracted with ethyl acetate. The obtained organic layer was washed with saturated brine, dried over anhydrous magnesium sulfate, and filtered. The filtrate was concentrated under reduced pressure. The obtained concentrate was purified by silica gel column chromatography to obtain 0.90 g of the title compound (yield: 84%).

$^1$H-NMR of the obtained title compound will be shown below.

$^1$H-NMR (CDCl$_3$) δ: 8.50 (1H, d), 7.83 (1H, d), 3.07 (2H, q), 1.41 (3H, t).

(Step 2) Synthesis of 5-bromo-3-(ethylsulfonyl)picolinonitrile

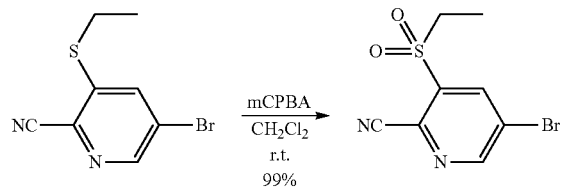

5-Bromo-3-(ethylthio)picolinonitrile (149 g) was dissolved in dichloromethane (1800 ml), and the solution was cooled to 0° C. and stirred. 70% m-chloroperbenzoic acid (333 g) was added thereto, and the mixture was stirred overnight at room temperature. The obtained solution was poured into a mixed solution of a saturated aqueous solution of sodium bicarbonate and a saturated aqueous solution of sodium thiosulfate, and extracted with dichloromethane. The obtained organic layer was washed with saturated brine, dried over anhydrous magnesium sulfate, and filtered. The filtrate was concentrated under reduced pressure. The obtained concentrate was purified by silica gel column chromatography to obtain 167 g of the title compound (yield: 99%).

$^1$H-NMR of the obtained title compound will be shown below.

$^1$H-NMR (CDCl$_3$) δ: 9.26 (1H, d), 8.72 (1H, d), 3.60 (2H, q), 1.23 (3H, t).

(Step 3) Synthesis of 2-(5-bromo-3-(ethylsulfonyl)pyridin-2-yl)-1-methyl-1H-imidazole-5-carbaldehyde

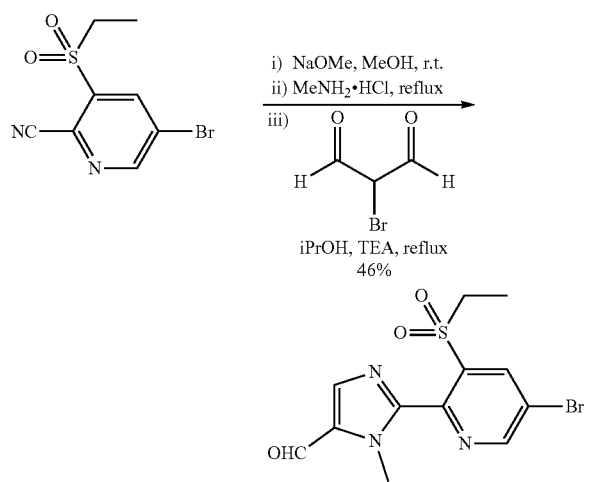

5-Bromo-3-(ethylsulfonyl)picolinonitrile (20 g) was dissolved in methanol (220 ml). To the solution, a ca. 5 M solution of sodium methoxide in methanol (1.5 ml) was added dropwise, and the mixture was stirred overnight at room temperature. Methylamine hydrochloride (4.9 g) was added thereto, and the mixture was heated and stirred for hours under reflux. Triethylamine (30 ml) was added thereto to obtain solution A.

Aside from this, 5-bromomalonaldehyde (16.5 g) and isopropanol (220 ml) were mixed and stirred at 50° C. for 1 hour to obtain solution B.

The solution B was added dropwise to the solution A, and the mixture was heated and stirred for 4 hours under reflux. The obtained solution was concentrated under reduced pressure. The obtained residue was added to water, and extracted with ethyl acetate. The obtained organic layer was washed with saturated brine, dried over anhydrous magnesium sulfate, and filtered. The filtrate was concentrated under reduced pressure. The obtained concentrate was purified by silica gel column chromatography to obtain 12 g of the title compound (yield: 46%).

$^1$H-NMR of the obtained title compound will be shown below.

$^1$H-NMR (CDCl$_3$) δ: 9.86 (1H, s), 9.00 (1H, d), 8.62 (1H, d), 7.83 (1H, s), 3.89 (3H, s), 3.79 (2H, q), 1.36 (3H, t).

(Step 4) Synthesis of 2-(5-cyclopropyl-3-(ethylsulfonyl)pyridin-2-yl)-1-methyl-1H-imidazole-5-carbaldehyde

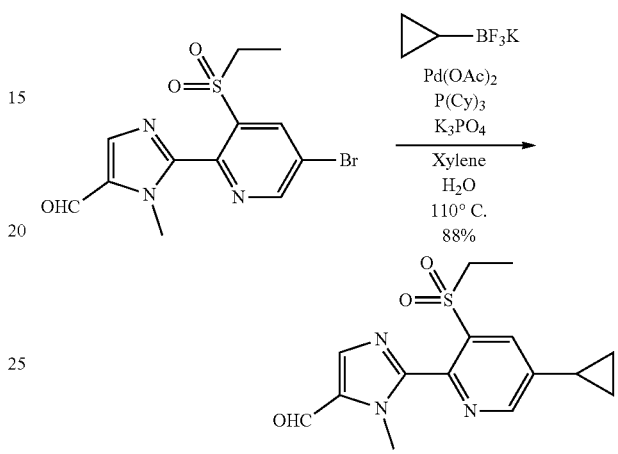

In a reaction vessel, 2-(5-bromo-3-(ethylsulfonyl)pyridin-2-yl)-1-methyl-1H-imidazole-5-carbaldehyde (0.35 g) was dissolved in xylene (4.3 ml), and the reaction vessel was replaced with argon. Then, the solution was stirred at room temperature. Potassium cyclopropyl trifluoroborate (0.36 g), palladium(II) acetate (0.043 g), a solution of 20% tricyclohexylphosphine in toluene (0.54 g), tripotassium phosphate (0.82 g), and water (0.48 ml) were added thereto, and the mixture was stirred at 110° C. for 7 hours. The obtained solution was poured into water, and extracted with ethyl acetate. The obtained organic layer was washed with saturated brine, dried over anhydrous magnesium sulfate, and filtered. The filtrate was concentrated under reduced pressure. The obtained concentrate was purified by silica gel column chromatography to obtain 0.27 g of the title compound (yield: 88%).

$^1$H-NMR of the obtained title compound will be shown below.

$^1$H-NMR (CDCl$_3$) δ: 9.84 (1H, s), 8.70 (1H, d), 8.02 (1H, d), 7.82 (1H, s), 3.84 (3H, s), 3.70 (2H, q), 2.12-2.06 (1H, m), 1.31 (3H, t), 1.28-1.23 (2H, m), 0.95-0.91 (2H, m).

(Step 5) Synthesis of 2-(5-(2-chloro-3,3,3-trifluoroprop-1-en-1-yl)-1-methyl-1H-imidazol-2-yl)-5-cyclopropyl-3-(ethylsulfonyl)pyridine

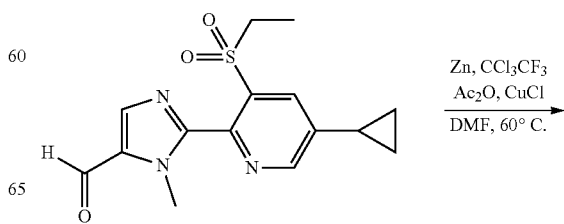

-continued

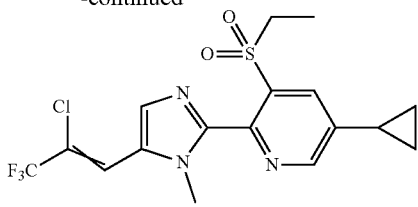

In a reaction vessel, 2-(5-cyclopropyl-3-(ethylsulfonyl) pyridin-2-yl)-1-methyl-1H-imidazole-5-carbaldehyde (0.3 g) was dissolved in N,N-dimethylformamide (13 ml), and the solution was stirred at room temperature. 1,1,1-Trichloro-2,2,2-trifluoroethane (0.35 g), a zinc powder (0.31 g), acetic anhydride (0.14 g), and copper chloride (4.7 mg) were added thereto, and the reaction vessel was replaced with argon, followed by stirring overnight at 60° C. The obtained solution was poured to a 10% aqueous Rochelle salt solution, and extracted with ethyl acetate. The obtained organic layer was washed with saturated brine, dried over anhydrous magnesium sulfate, and filtered. The filtrate was concentrated under reduced pressure. The obtained concentrate was purified by silica gel column chromatography to obtain 0.23 g of the title compound (E/Z=17:83, yield: 59%).

$^1$H-NMR and $^{19}$F-NMR of the obtained title compound will be shown below.

$^1$H-NMR (400 MHz, CDCl$_3$) (an E/Z mixture) δ: 8.68 (1H, d), 8.04 (1H, s), 8.02 (1H, d), 7.15 (1H, s), 3.74 (2H, q), 3.57 (3H, s), 2.12-2.06 (1H, m), 1.31 (3H, t), 1.28-1.20 (2H, m), 0.94-0.89 (2H, m); $^{19}$F-NMR (376 MHz, CDCl$_3$—C$_6$F$_6$): δ −63.5(d) for the (E)-isomer and −68.4(s) for the (Z)-isomer.

Example 2

Synthesis of 1-(6-(5-(2-chloro-3,3,3-trifluoroprop-1-en-1-yl)-1-methyl-1H-imidazol-2-yl)-5-(ethylsulfonyl)pyridin-3-yl)cyclopropane-1-carbonitrile (Compound No. d-15)

(Step 1) Synthesis of 2-(5-(1,3-dioxolan-2-yl)-1-methyl-1H-imidazol-2-yl)-5-bromo-3-(ethylsulfonyl) pyridine

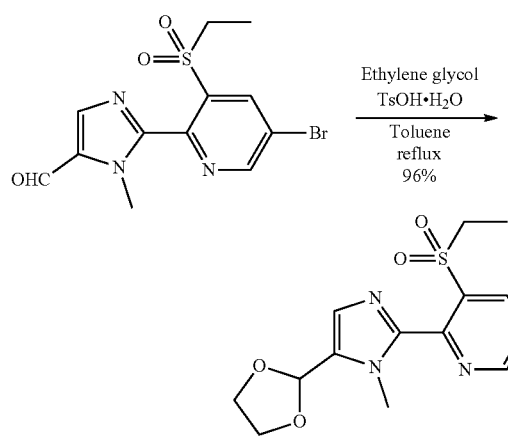

2-(5-Bromo-3-(ethylsulfonyl)pyridin-2-yl)-1-methyl-1H-imidazole-5-carbaldehyde (8.0 g) was dissolved in toluene (150 ml), and the solution was stirred at room temperature. Ethylene glycol (17 g) and p-toluenesulfonic acid monohydrate (0.84 g) were added thereto, and the mixture was heated and stirred overnight under reflux using a Dean-Stark apparatus. The obtained solution was poured into a saturated aqueous solution of sodium bicarbonate, and extracted with chloroform. The obtained organic layer was washed with saturated brine, dried over anhydrous magnesium sulfate, and filtered. The filtrate was concentrated under reduced pressure. The obtained concentrate was purified by silica gel column chromatography to obtain 8.5 g of the title compound (yield: 96%).

$^1$H-NMR of the obtained title compound will be shown below.

$^1$H-NMR (CDCl$_3$) δ: 8.94 (1H, d), 8.60 (1H, d), 7.19 (1H, s), 6.02 (1H, s), 4.17-4.00 (4H, m), 3.86 (2H, q), 3.64 (3H, s), 1.33 (3H, t).

(Step 2) Synthesis of 2-(6-(5-(1,3-dioxolan-2-yl)-1-methyl-1H-imidazol-2-yl)-5-(ethylsulfonyl)pyridin-3-yl)acetonitrile

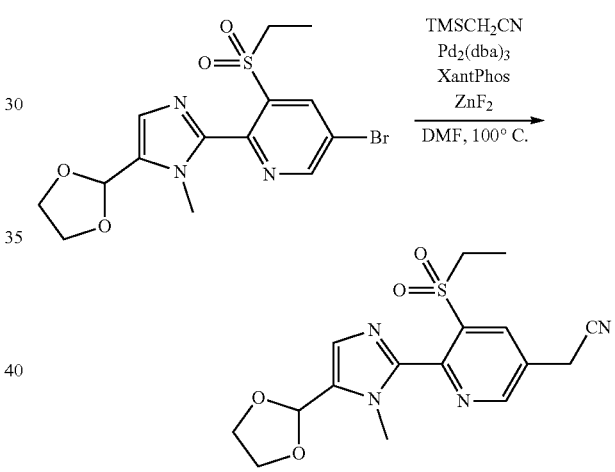

In a reaction vessel, 2-(5-(1,3-dioxolan-2-yl)-1-methyl-1H-imidazol-2-yl)-5-bromo-3-(ethylsulfonyl)pyridine (1.75 g) was dissolved in N,N-dimethylformamide (23 ml), and the reaction vessel was replaced with argon. Then, the solution was stirred at room temperature. Trimethylsilylacetonitrile (0.98 g), tris(dibenzylideneacetone)dipalladium(0) (0.40 g), xantphos (0.50 g), and zinc fluoride (0.27 g) were added thereto, and the mixture was stirred at 100° C. for 3 hours. The obtained solution was poured into a saturated aqueous solution of ammonium chloride, and extracted with ethyl acetate. The obtained organic layer was washed with saturated brine, dried over anhydrous magnesium sulfate, and filtered. The filtrate was concentrated under reduced pressure. The obtained concentrate was purified by silica gel column chromatography to obtain 0.51 g of the title compound (yield: 42%).

$^1$H-NMR of the obtained title compound will be shown below.

$^1$H-NMR (CDCl$_3$) δ: 8.98-8.87 (1H, m), 8.46-8.39 (1H, m), 7.21 (1H, s), 6.03 (1H, s), 4.18-4.02 (4H, m), 3.96-3.93 (2H, m), 3.87 (2H, q), 3.65 (3H, s), 1.33 (3H, t).

(Step 3) Synthesis of 1-(6-(5-(1,3-dioxolan-2-yl)-1-methyl-1H-imidazol-2-yl)-5-(ethylsulfonyl)pyridin-3-yl)cyclopropane-1-carbonitrile

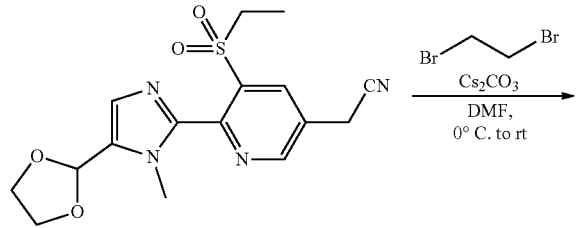

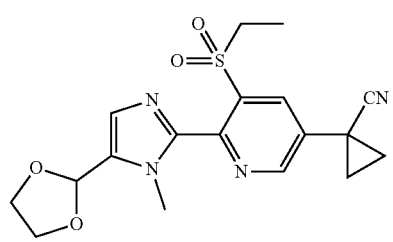

2-(6-(5-(1,3-Dioxolan-2-yl)-1-methyl-1H-imidazol-2-yl)-5-(ethylsulfonyl)pyridin-3-yl)acetonitrile (0.50 g) was dissolved in N,N-dimethylformamide (5 ml), and the solution was stirred at 0° C. Cesium carbonate (0.45 g) was added thereto. Then, 1,2-dibromoethane (0.52 g) was added dropwise thereto, and the mixture was stirred at 0° C. for 20 minutes. Cesium carbonate (0.90 g) was added thereto, and the mixture was stirred at room temperature for 3 hours. The obtained solution was poured into water, and extracted with ethyl acetate. The obtained organic layer was washed with saturated brine, dried over anhydrous magnesium sulfate, and filtered. The filtrate was concentrated under reduced pressure. The obtained concentrate was purified by silica gel column chromatography to obtain 0.29 g of the title compound (yield: 54%).

$^1$H-NMR of the obtained title compound will be shown below.

$^1$H-NMR (CDCl$_3$) δ: 8.97 (1H, d), 8.17 (1H, d), 7.19 (1H, s), 6.02 (1H, s), 4.18-4.01 (4H, m), 3.85 (2H, q), 3.64 (3H, s), 1.97 (2H, dd), 1.61 (2H, dd), 1.31 (3H, t).

(Step 4) Synthesis of 1-(5-(ethylsulfonyl)-6-(5-formyl-1-methyl-1H-imidazol-2-yl)pyridin-3-yl)cyclopropane-1-carbonitrile

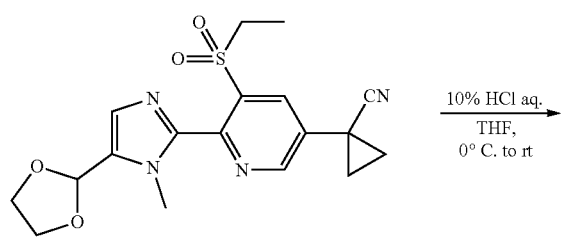

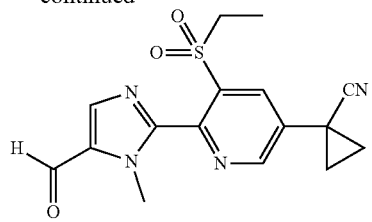

1-(6-(5-(1,3-Dioxolan-2-yl)-1-methyl-1H-imidazol-2-yl)-5-(ethylsulfonyl)pyridin-3-yl)cyclopropane-1-carbonitrile (0.24 g) was dissolved in tetrahydrofuran (10 ml), and the solution was stirred at 0° C. 10% hydrochloric acid (2 ml) was added thereto, and the mixture was stirred at room temperature for 3 hours. The obtained solution was poured into a saturated aqueous solution of sodium bicarbonate, and extracted with ethyl acetate. The obtained organic layer was washed with saturated brine, dried over anhydrous magnesium sulfate, and filtered. The filtrate was concentrated under reduced pressure. The obtained concentrate was purified by silica gel column chromatography to obtain 0.23 g of the title compound (yield: 54%).

$^1$H-NMR of the obtained title compound will be shown below.

$^1$H-NMR (CDCl$_3$) δ: 9.86 (1H, s), 9.00 (1H, d), 8.20 (1H, d), 7.83 (1H, s), 3.88 (3H, s), 3.79 (2H, dd), 2.01 (2H, dd), 1.64 (2H, dd), 1.34 (3H, t).

(Step 5) Synthesis of 1-(6-(5-(2-chloro-3,3,3-trifluoroprop-1-en-1-yl)-1-methyl-1H-imidazol-2-yl)-5-(ethylsulfonyl)pyridin-3-yl)cyclopropane-1-carbonitrile In a reaction vessel, 1-(5-(ethylsulfonyl)-6-(5-formyl-1-methyl-1H-imidazol-2-yl)pyridin-3-yl)cyclopropane-1-carbonitrile (0.23 g) was dissolved in N,N-dimethylformamide (10 ml), and the solution was stirred at room temperature. 1,1,1-Trichloro-2,2,2-trifluoroethane (3.1 g), a zinc powder (2.0 g), acetic anhydride (1.0 g), and copper chloride (3.0 mg) were added thereto, and the reaction vessel was replaced with argon, followed by stirring overnight at 60° C. The obtained solution was poured to a saturated aqueous solution of sodium bicarbonate, and extracted with ethyl acetate. The obtained organic layer was washed with saturated brine, dried over anhydrous magnesium sulfate, and filtered. The filtrate was concentrated under reduced pressure. The obtained concentrate was purified by silica gel column chromatography to obtain 0.09 g of the title compound (E/Z=18:82, yield: 30%).

$^1$H-NMR and $^{19}$F-NMR of the obtained title compound will be shown below.

$^1$H-NMR (400 MHz, CDCl$_3$) (an E/Z mixture) δ: 8.99 (1H, d), 8.19 (1H, d), 8.05 (1H, s), 7.16 (1H, s), 3.85 (2H, q), 3.63 (3H, s), 2.00 (2H, dd), 1.63 (2H, dd), 1.34 (3H, t); $^{19}$F-NMR (376 MHz, CDCl$_3$—C$_6$F$_6$): δ −63.5 (s) for the (E)-isomer and −68.5 (s) for the (Z)-isomer.

Some compounds of the present invention produced in the same way as in Examples described above are shown in Tables 1 and 2. Table 1 shows the substituents of the compound represented by the formula (I). In the tables, properties or melting point (m.p.) are also shown as the physical properties of each compound.

In Table 1, Me represents a methyl group, Et represents an ethyl group, $^c$Pr represents a cyclopropyl group, and $^c$Pen represents a cyclopentyl group.

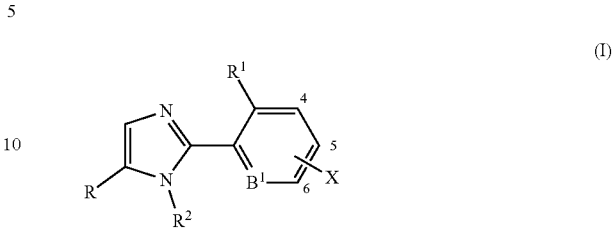

(I)

TABLE 1

| Compound No. | X | B$^1$ | R$^1$ | R$^2$ | R | Configuration | Physical properties |
|---|---|---|---|---|---|---|---|
| d-1 | 5-$^c$Pr | N | SO$_2$Et | Me | CH=CHCF$_2$CF$_3$ | E | m.p.: 142-143(° C.) |
| d-2 | 5-$^c$Pr | N | SO$_2$Et | Me | CH=C(Cl)CF$_3$ | E/Z | m.p.: 180-182(° C.) |
| d-3 | 5-$^c$Pr | CH | SO$_2$Et | Me | CH=CHCF$_2$CF$_2$CF$_3$ | E | m.p.: 149-151(° C.) |
| d-4 | 5-$^c$Pr | N | SO$_2$Et | Me | CH=CHCF$_2$CF$_2$CF$_2$CF$_3$ | E | m.p.: 110-112(° C.) |
| d-5 | 5-$^c$Pr | CH | SO$_2$Et | Me | CH=CHCF$_2$CF$_3$ | E | m.p.: 154-156(° C.) |
| d-6 | 5-$^c$Pr | CH | SEt | Me | CH=C(Cl)CF$_3$ | E/Z | viscous oil |
| d-7 | 5-$^c$Pr | CH | SO$_2$Et | Me | CH=C(Cl)CF$_3$ | E/Z | m.p.: 170-172(° C.) |
| d-8 | 5-$^c$Pr | N | SO$_2$Et | Me | CH=CCl$_2$ | — | m.p.: 159-161(° C.) |
| d-9 | 5-$^c$Pr | N | SO$_2$Et | Me | CH=C(F)CF$_2$CF$_3$ | Z | m.p.: 122-124(° C.) |
| d-10 | 5-$^c$Pr | N | SO$_2$Et | Me | CH=C(F)CF$_2$CF$_3$ | E | m.p.: 151-153(° C.) |
| d-11 | 5-$^c$Pr | N | SO$_2$Et | Me | CH=CBrF | E | m.p.: 148-150(° C.) |
| d-12 | 5-$^c$Pr | N | SO$_2$Et | Me | CH=C(Cl)CF$_2$CF$_3$ | Z | m.p.: 117-119(° C.) |
| d-13 | 5-$^c$Pr | N | SO$_2$Et | Me | CH=C(Cl)CF$_2$CF$_2$CF$_3$ | Z | m.p.: 103-105(° C.) |
| d-14 | 5-$^c$Pr | N | SO$_2$Et | Me | CH=C(I)Cl | E | m.p.: 121-123(° C.) |
| d-15 | 5-(1-CN-$^c$Pr) | N | SO$_2$Et | Me | CH=C(Cl)CF$_2$ | E/Z | m.p.: 65-68(° C.) |
| d-16 | 5-(1-CN-$^c$Pr) | N | SO$_2$Et | Me | CH=CHCF$_3$ | E | amorphous |
| d-17 | 5-(1-(CONH$_2$)-$^c$Pr) | N | SO$_2$Et | Me | CH=C(Cl)CF$_3$ | E/Z | m.p.: 205-207(° C.) |
| d-18 | 5-(1-(CSNH$_2$)-$^c$Pr) | N | SO$_2$Et | Me | CH=C(Cl)CF$_3$ | E/Z | m.p.: 215-217(° C.) |
| d-19 | 5-$^c$Pr | N | SO$_2$Et | Me | CH=C(CF$_3$)$_2$ | — | m.p.: 182-186(° C.) |
| d-20 | 5-(1-Me-$^c$Pr) | N | SO$_2$Et | Me | CH=C(Cl)CF$_3$ | E/Z | m.p.: 137-139(° C.) |
| d-21 | 5-(1-(pyridin-2-yl)-cPr) | N | SO$_2$Et | Me | CH=C(Cl)CF$_3$ | E/Z | m.p.: 157-159(° C.) |
| d-22 | 5-(1-CN-$^c$Pr) | N | SO$_2$Et | Me | CH=CHCF$_3$ | E | m.p.: 158-160(° C.) |
| d-23 | 5-(1-CN-$^c$Pr) | N | SO$_2$Et | Me | CH=CHCF$_2$CF$_3$ | E | m.p.: 140-142(° C.) |
| d-24 | 5-$^c$Pr | N | SO$_2$Et | Me | CH=C(Br)CF$_3$ | E/Z | m.p.: 166-168(° C.) |
| d-25 | 5-$^c$Pr | N | SO$_2$Et | Me | CH=CHCF$_2$CF$_3$ | E | m.p.: 143-145(° C.) |
| d-26 | 5-(1-Me-$^c$Pr) | N | SO$_2$Et | Me | CH=CHCF$_2$CF$_3$ | E | m.p.: 94-97(° C.) |
| d-27 | 5-$^c$Pr | N | SO$_2$Et | Me | CH=C(F)CF$_2$CF$_2$CF$_3$ | Z | m.p.: 106-108(° C.) |
| d-28 | 5-$^c$Pr | N | SO$_2$Me | Me | CH=C(Cl)CF$_3$ | E/Z | m.p.: 196-198(° C.) |
| d-29 | 5-(1-Me-$^c$Pr) | N | SO$_2$Et | Me | CH=CHCF$_2$CF$_3$ | E | m.p.: 153-155(° C.) |
| d-30 | 5-$^c$Pr | N | SO$_2$Me | Me | CH=C(Cl)CF$_2$CF$_3$ | Z | m.p.: 151-153(° C.) |
| d-31 | 5-(1-Me-$^c$Pr) | N | SO$_2$Et | Me | CH=C(F)CF$_2$CF$_3$ | Z | m.p.: 119-121(° C.) |
| d-32 | 5-$^c$Pen | N | SO$_2$Et | Me | CH=C(Cl)CF$_3$ | E/Z | m.p.: 142-144(° C.) |
| d-33 | 5-$^c$Pr | N | SO$_2$Et | Me | CH=C(Cl)CF$_3$ | E | m.p.: 159-161(° C.) |
| d-34 | 5-$^c$Pr | N | SO$_2$Et | Me | CH=C(Cl)CF$_3$ | Z | m.p.: 169-171(° C.) |
| d-35 | 5-$^c$Pr | N | SO$_2$Et | Me | CF=C(F)OCF$_2$CF$_2$CF$_3$ | Z | m.p.: 113-115(° C.) |
| d-36 | 5-$^c$Pr | N | SO$_2$Et | Me | CF=C(F)OCF$_2$CF$_2$CF$_3$ | E | m.p.: 131-133(° C.) |
| d-37 | 5-$^c$Pr | N | SO$_2$Et | Me | CF=C(F)OCF$_3$ | E/Z | m.p.: 113-116(° C.) |

TABLE 2

| Compound No. | Structure | Configuration | Physical properties |
|---|---|---|---|
| e-1 | 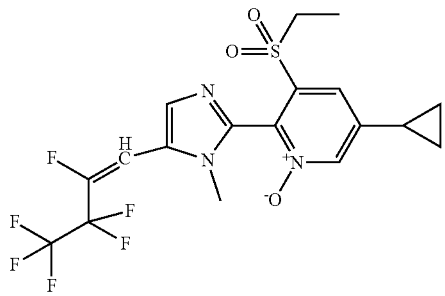 | Z | m.p.: 121-123 (° C.) |
| e-2 | 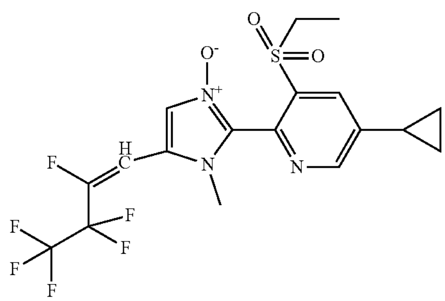 [SMILES: CCS(=O)(=O)c1cc(C2CC2)cnc1-c1n(C)c(/C=C(/F)C(F)(F)C(F)(F)F)c[n+]1[O-]] | Z | m.p.: 190-192 (° C.) |
| e-3 | 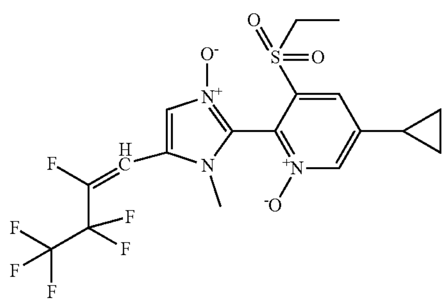 | Z | m.p.: 244-246 (° C.) |
| e-4 | 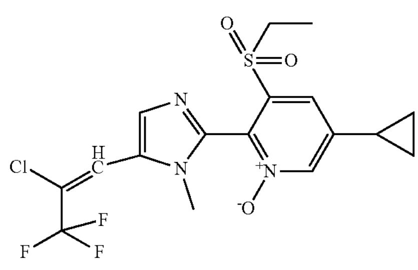 | E/Z | m.p.: 143-145 (° C.) |
| e-5 | 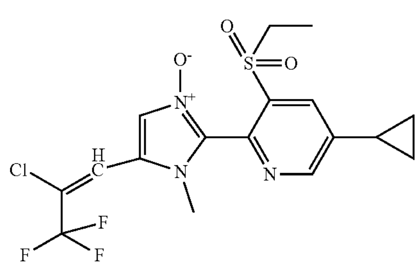 [SMILES: CCS(=O)(=O)c1cc(C2CC2)cnc1-c1n(C)c(/C=C(/Cl)C(F)(F)F)c[n+]1[O-]] | E/Z | m.p.: 221-225 (° C.) |

TABLE 2-continued

| Compound No. | Structure | Configuration | Physical properties |
|---|---|---|---|
| e-6 | 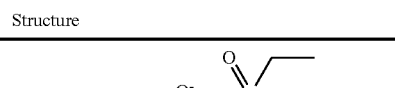 | E/Z | m.p.: 257-262 (° C.) |

The ¹H-NMR data of compounds having physical properties of viscous oil or amorphous among the compounds shown in Table 1 will be shown below.

Compound No. d-6: 1H-NMR (400 MHz, CDCl3): d 8.08 (s, 1H), 7.48 (s, 1H), 7.23 (d, 1H), 7.15 (d, 1H), 6.94 (dd, 1H), 3.47 (s, 3H), 3.42 (s, 3H), 2.79 (q, 2H), 1.98-1.90 (m, 1H), 1.22 (t, 3H), 1.21 (t, 3H), 1.07-1.02 (m, 2H), 0.78-0.84 (m, 2H).

Compound No. d-16: 1H-NMR (400 MHz, CDCl3): d 8.99 (d, 1H), 8.19 (d, 1H), 7.47 (s, 1H), 7.05-6.98 (m, 1H), 6.22-6.13 (m, 1H), 3.86 (q, 3H), 3.62 (s, 3H), 2.01-1.97 (m, 2H), 1.64-1.60 (m, 2H), 1.34 (t, 3H).

[Biological Test]

Test Examples given below show that the (hetero)aryl imidazole compound of the present invention is useful as an active ingredient for pest control agents and ectoparasite control agents. The term "part" is based on weight.

(Preparation of Test Emulsion)

5 parts of the (hetero)aryl imidazole compound of the present invention, 93.6 parts of dimethylformamide, and 1.4 parts of polyoxyethylene alkyl aryl ether were mixed and dissolved to prepare emulsion (I) containing 5% of the active ingredient.

For a control, 98.5 parts of dimethylformamide and 1.5 parts of polyoxyethylene alkyl aryl ether were mixed and dissolved to prepare emulsion (II).

An insecticidal rate was calculated according to the following expression:

Insecticidal rate (%)=(The number of dead insects/The number of tested insects)×100

Test Example 1

Test of Efficacy on *Mythimna separata*

0.8 g of commercially available artificial feed (Insecta LFS, manufactured by Nosan Corp.) and 1 μl of the emulsion (I) were well mixed to obtain test feed.

A plastic test container (capacity: 1.4 ml) was packed with 0.2 g of the test feed per treatment plot. Then, two second instar larvae of *Mythimna separata* were inoculated to each treatment plot. A plastic lid was put on the test container so as to prevent escape of the second instar larvae of *Mythimna separata*. The container was placed in a thermostat chamber of 25° C. On the fifth day, the insecticidal rate and the food intake were examined. The test was conducted in duplicate.

The insecticidal rate and the food intake of a control plot were examined in the same way as in Test Example 1 except that the emulsion (I) was changed to the emulsion (II).

Compounds of compound Nos. d-1, d-2, d-3, d-4, d-5, d-6, d-7, d-8, d-1, d-12, d-13, d-14, d-15, d-16, d-18, d-19, d-20, d-21, d-22, d-23, d-24, d-27, d-28, d-29, d-30, d-32, d-33, d-34, d-35, d-36, d-37, e-1 and e-4 were tested for their efficacy on *Mythimna separata*. All the compounds had an insecticidal rate of 100% for *Mythimna separata* or a food intake of 10% or less as compared with the control plot. As is evident, the (hetero)aryl imidazole compound of the present invention is effective for *Mythimna separata*.

Test Example 2

Test of Efficacy on *Mythimna separata*

The emulsion (I) was diluted with water such that the concentration of the compound of the present invention was 125 ppm. Corn leaves were dipped in the dilution for seconds. The resulting corn leaves were placed in a petri dish, and five second instar larvae of *Mythimna separata* were released. The petri dish was placed in a thermostat chamber having a temperature of 25° C. and a humidity of 60%. Life and death were determined after 6 days from the release of the insects, and the insecticidal rate was calculated. The test was conducted in duplicate.

Compounds of compound Nos. d-1, d-2 and d-15 were tested for their efficacy on *Mythimna separata*. All the compounds exhibited an insecticidal rate of 80% or more for *Mythimna separata*.

Test Example 3

Test of Efficacy on *Plutella xylostella*

The emulsion (I) was diluted with water such that the concentration of the compound of the present invention was 125 ppm. Cabbage leaves were dipped in the dilution for 30 seconds. The resulting cabbage leaves were placed in a petri dish. Five second instar larvae of *Plutella xylostella* were released thereto. The petri dish was placed in a thermostat chamber having a temperature of 25° C. and a humidity of 60%. Life and death were determined after 3 days from the release of the insects, and the insecticidal rate was calculated. The test was conducted in duplicate.

Compounds of compound Nos. d-1, d-2, d-4, d-7, d-9, d-10, d-12, d-13, d-15, d-18, d-20, d-21, d-22, d-23, d-24, d-25, d-26, d-27, d-28, d-29, d-30, d-31, d-33 and d-34 were tested for their efficacy on *Plutella xylostella*. All the compounds exhibited an insecticidal rate of 80% or more for *Plutella xylostella*.

Test Example 4

Test of Efficacy on *Spodoptera litura*

The emulsion (I) was diluted with water such that the concentration of the compound of the present invention was 125 ppm. Cabbage leaves were dipped in the dilution for 30 seconds. The resulting cabbage leaves were placed in a petri dish, and five second instar larvae of *Spodoptera litura* were released. The petri dish was placed in a thermostat chamber having a temperature of 25° C. and a humidity of 60%. Life and death were determined after 6 days from the release of the insects, and the insecticidal rate was calculated. The test was conducted in duplicate.

Compounds of compound Nos. d-2, d-12 and d-15 were tested for their efficacy on *Spodoptera litura*. All the compounds exhibited an insecticidal rate of 80% or more for *Spodoptera litura*.

Test Example 5

Test of Efficacy on *Aphis craccivora*

Seedlings of black-eyed peas were raised in 10-cm pots. *Aphis craccivora* nymphs were inoculated onto primary leaves. The emulsion (I) was diluted with water such that the concentration of the compound of the present invention was 125 ppm. The dilution was sprayed to the black-eyed peas parasitized by the *Aphis craccivora* nymphs. The black-eyed peas were placed in a thermostat chamber having a temperature of 25° C. and a humidity of 60%. Life and death of *Aphis craccivora* were determined after 4 days from the spraying, and the insecticidal rate was calculated. The test was conducted in duplicate.

Compounds of compound Nos. d-1, d-2, d-3, d-4, d-5, d-6, d-7, d-8, d-11, d-12, d-13, d-15, d-16, d-17, d-18, d-20, d-21, d-22, d-23, d-24, d-25, d-27, d-29, d-30, d-32, d-34, d-35, d-36, d-37 and e-1 were tested for their efficacy on Aphis craccivora. All the compounds exhibited an insecticidal rate of 80% or more for *Aphis craccivora*.

Test Example 6

Test of Efficacy on *Phyllotreta striolata*

The emulsion (I) was diluted with water such that the concentration of the compound of the present invention was 125 ppm to prepare a test chemical. The test chemical was sprayed to Qing geng cai seedlings (at the seventh true leaf stage) planted in 10-cm pots. The Qing geng cai seedlings were dried in air and then placed in a plastic cup. Ten *Phyllotreta striolata* adults were released thereto. The plastic cup was stored in a thermostat chamber having a temperature of 25° C. and a humidity of 65%. Life and death were determined after 7 days from the release of the insects, and the insecticidal rate was calculated. The test was conducted in duplicate.

Compounds of compound Nos. d-1, d-2, d-4, d-9, d-10, d-12, d-13, d-15, d-18, d-20, d-22, d-23, d-25, d-26, d-27, d-29, d-31, d-33, d-34 and e-2 were tested for their efficacy on Phyllotreta striolata adults. All the compounds exhibited an insecticidal rate of 80% or more for *Phyllotreta striolata* adults.

Test Example 7

Test of Efficacy on *Nilaparvata lugens*

The emulsion (I) was diluted with water such that the concentration of the compound of the present invention was 125 ppm. Young seedlings of rice were dipped in the dilution for 30 seconds. The young seedlings of rice were dried in air and then placed in a plastic case. Five second instar larvae of *Nilaparvata lugens* were released thereto. The plastic case was stored in a thermostat chamber having a temperature of 25° C. and a humidity of 65%. Life and death were determined after 7 days from the inoculation, and the insecticidal rate was calculated. The test was conducted in duplicate.

Compounds of compound Nos. d-1, d-2, d-9, d-13, d-15, d-18, d-22, d-23, d-25, d-26, d-30 and d-31 were tested for their efficacy on *Nilaparvata lugens*. All the compounds exhibited an insecticidal rate of 80% or more for *Nilaparvata lugens*.

Test Example 8

Test of Efficacy on *Musca domestica*

The compound of the present invention was diluted with acetone and the dilution was added dropwise at 100 ppm of the compounds of the present invention per g of a cube of sugar. The cube of sugar was placed in a plastic cup. Ten female adults of Musca domestica were released, and a lid was put on the plastic cup. The plastic cup was stored at 25° C. Life and death were determined after 24 hours from the release of the insects, and the insecticidal rate was calculated. The test was conducted in duplicate.

A compound of compound No. b-4 was tested for its efficacy on *Musca domestica*. The compound exhibited an insecticidal rate of 80% or more for *Musca domestica*.

Test Example 9

Test of Efficacy on *Aphis gossypii*

Cucumber seedlings raised in 10-cm pots were pulled out of the 10-cm pots. Soil attached to the root portions was washed off with tap water, and the root portions were dipped in tap water, followed by hydroponic culture. *Aphis gossypii* nymphs were inoculated onto the cucumber seedlings. The emulsion (I) was diluted with water such that the concentration of the compound of the present invention was 31 ppm to obtain a dilution. The tap water was replaced with the dilution, and the hydroponic culture was continued with the dilution in a thermostat chamber having a temperature of 25° C. and a humidity of 60%. Life and death of Aphis gossypii were determined after 6 days from the start of the hydroponic culture with the dilution, and the insecticidal rate was calculated. The test was conducted in duplicate.

Compounds of compound Nos. d-1, d-2, d-9, d-15, d-18, d-26, d-27 and d-33 were tested for their efficacy on *Aphis gossypii*. All the compounds exhibited an insecticidal rate of 80% or more for *Aphis gossypii*.

Test Example 10

Test of Efficacy on *Phyllotreta striolata*

The emulsion (I) was diluted with water such that the concentration of the compound of the present invention was 31 ppm to prepare a test chemical. The test chemical was sprayed to Qing geng cai seedlings (at the seventh true leaf stage) planted in 10-cm pots. The Qing geng cai seedlings were dried in air and then placed in a plastic cup. Ten *Phyllotreta striolata* adults were released thereto. The plastic cup was stored in a thermostat chamber having a temperature of 25° C. and a humidity of 65%. Life and death were determined after 7 days from the release of the insects, and the insecticidal rate was calculated. The test was conducted in duplicate.

Compounds of compound Nos. d-1, d-2, d-4, d-9, d-10, d-12, d-13, d-15, d-18, d-20, d-22, d-23, d-25, d-26, d-27, d-29, d-33, d-34 and e-2 were tested for their efficacy on *Phyllotreta striolata* adults. All the compounds exhibited an insecticidal rate of 80% or more for *Phyllotreta striolata* adults.

All the compounds selected at random from among the (hetero)aryl imidazole compounds of the present invention exerted the effect as described above. It may therefore be understood that the (hetero)aryl imidazole compound of the present invention, including unillustrated compounds, is a compound having an effect such as a pest control effect, particularly, an acaricidal or insecticidal effect. It may also be understood that the (hetero)aryl imidazole compound of the present invention is a compound also having an effect on parasites harmful to humans and animals, such as ectoparasites.

The invention claimed is:

1. A compound represented by formula (IV), an N-oxide compound, stereoisomer, tautomer or hydrate thereof or a salt of any of these compounds:

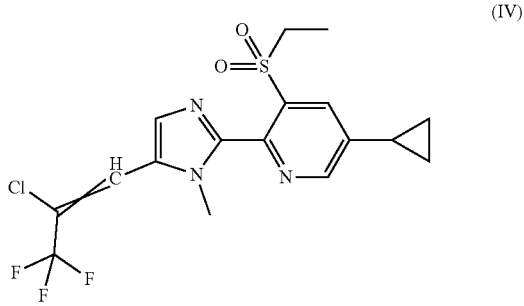 [SMILES: CCS(=O)(=O)c1cc(C2CC2)cnc1-c1ncc(C=C(Cl)C(F)(F)F)n1C]

(IV)

wherein the carbon-carbon double stereo bond represents an E form or a Z form, or a mixture thereof.

2. A pest control agent comprising at least one compound selected from the group consisting of a compound according to claim 1, an N-oxide compound, stereoisomer, tautomer and hydrate thereof and a salt of any of these compounds, as an active ingredient.

3. An insecticide or acaricide comprising at least one compound selected from the group consisting of a compound according to claim 1, an N-oxide compound, stereoisomer, tautomer and hydrate thereof and a salt of any of these compounds, as an active ingredient.

4. An ectoparasite control agent comprising at least one compound selected from the group consisting of a compound according to claim 1, an N-oxide compound, stereoisomer, tautomer and hydrate thereof and a salt of any of these compounds, as an active ingredient.

5. An endoparasite control agent or expellant comprising at least one compound selected from the group consisting of a compound according to claim 1, an N-oxide compound, stereoisomer, tautomer and hydrate thereof and a salt of any of these compounds, as an active ingredient.

6. A seed treatment agent or vegetative propagation organ treatment agent comprising at least one compound selected from the group consisting of a compound according to claim 1, an N-oxide compound, stereoisomer, tautomer and hydrate thereof and a salt of any of these compounds, as an active ingredient.

7. A granular agrochemical composition for paddy rice seedling nursery box treatment comprising at least one compound selected from the group consisting of a compound according to claim 1, an N-oxide compound, stereoisomer, tautomer and hydrate thereof and a salt of any of these compounds, as an active ingredient.

8. A soil treatment agent comprising at least one compound selected from the group consisting of a compound according to claim 1, an N-oxide compound, stereoisomer, tautomer and hydrate thereof and a salt of any of these compounds, as an active ingredient.

9. A bait agent comprising at least one compound selected from the group consisting of a compound according to claim 1, an N-oxide compound, stereoisomer, tautomer and hydrate thereof and a salt of any of these compounds, as an active ingredient.

10. A plant growth promoter comprising at least one compound selected from the group consisting of a compound according to claim 1, an N-oxide compound, stereoisomer, tautomer and hydrate thereof and a salt of any of these compounds, as an active ingredient.

* * * * *